US011230704B2

(12) United States Patent
Yamada et al.

(10) Patent No.: US 11,230,704 B2
(45) Date of Patent: Jan. 25, 2022

(54) OXIDATION OF HIGHLY UNSATURATED FATTY ACIDS WITH NOVEL 8-LIPOXYGENASE DERIVED FROM MALACOSTRACA

(71) Applicants: Bizen Chemical Co., Ltd., Akaiwa (JP); Iwate Prefectural Government, Morioka (JP)

(72) Inventors: Hidetoshi Yamada, Kitakami (JP); Sayaka Yuki, Kitakami (JP); Akira Yano, Kitakami (JP); Naomichi Bamba, Akaiwa (JP); Tadahiro Tsushima, Akaiwa (JP); Yoshihisa Misawa, Akaiwa (JP)

(73) Assignees: Bizen Chemical Co., Ltd., Akaiwa (JP); Iwate Prefectural Government, Morioka (JP)

( * ) Notice: Subject to any disclaimer, the term of this patent is extended or adjusted under 35 U.S.C. 154(b) by 0 days.

(21) Appl. No.: 16/976,431

(22) PCT Filed: Feb. 27, 2019

(86) PCT No.: PCT/JP2019/007659
§ 371 (c)(1),
(2) Date: Aug. 27, 2020

(87) PCT Pub. No.: WO2019/168060
PCT Pub. Date: Sep. 6, 2019

(65) Prior Publication Data
US 2021/0115411 A1    Apr. 22, 2021

(30) Foreign Application Priority Data
Feb. 28, 2018   (JP) ............................. JP2018-035760

(51) Int. Cl.
*C12N 9/02* (2006.01)
*C12P 7/64* (2006.01)

(52) U.S. Cl.
CPC .............. *C12N 9/0069* (2013.01); *C12P 7/64* (2013.01); *C12Y 113/11* (2013.01)

(58) Field of Classification Search
None
See application file for complete search history.

(56) References Cited

PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Accession A0A088B1G9. Nov. 26, 2014 (Year: 2014).*
Accession A0A1L7NZPO. Mar. 15, 2017 (Year: 2017).*
"Alox8," retrieved fromURL:https://web.archive.org/web/20170313173320/http://www.infomiatics.jax.org/marker/MGI:1098228, published on Mar. 13, 2017, 2 pages.
Baba et al., "Calcium Induces Membrane Translocation of 12-Lipoxygenase in Rat Platelets," *The Journal of Biological Chemistry* 264(27):15790-15795, 1989.
Brinckmann et al., "Membrane Translocation of 15-Lipoxygenase in Hematopoietic Cells Is Calcium-Dependent and Activates the Oxygenase Activity of the Enzyme," *Blood* 91(1):64-74, 1998.
Hashimoto et al., "n-3 fatty acids effectively improve the reference memory-related learning ability associated with increased brain docosahexaenoic acid-derived docosanoids in aged rats," *Biochimica et Biophysica Acta* 1851:203-209, 2015.
Klawitter et al., "Bioactive lipid mediators in polycystic kidney disease," *Journal of Lipid Research* 55:1139-1149, 2014.
UniProt/GeneSeq Accession No. A0A0P4WED2, retrieved from URL:https://www.uniprot.org/uniprot/A0A0P4WED2, published on Jan. 20, 2016, 5 pages.
Yamada et al., "Hydroxyeicosapentaenoic acids from the Pacific krill show high ligand activities for PPARs," *Journal of Lipid Research* 55:895-904, 2014.
Yamada et al., "Lipids, fatty acids and hydroxy-fatty acids of *Euphausia pacifica*," *Scientific Reports* 7:9944, 2017, 10 pages.
Yuki et al., "Identification of Lipoxygenase gene from pacific krill to use enzymatic production of 8-HEPE," *The 2018 Annual Meeting of The Japan Society for Bioscience, Biotechnology, and Agrochemistry*, Mar. 5, 2018, 5 pages (w/English Translation).
Zhang et al., "Integrating De Novo Transcriptome Assembly and Cloning to Obtain Chicken Ovocleidin-17 Full Length cDNA," *PLoS One* 9(3):e93452, 2014, 7 pages.

* cited by examiner

*Primary Examiner* — Christian L Fronda
(74) *Attorney, Agent, or Firm* — Seed IP Law Group LLP

(57) ABSTRACT

The present invention provides a lipoxygenase that enables the highly efficient formation of an oxide of a highly unsaturated fatty acid or an oxide of a highly unsaturated fatty acid derivative from a highly unsaturated fatty acid or a highly unsaturated fatty acid derivative. The present invention provides a lipoxygenase that enables the highly efficient formation of 8-hydroxyeicosatetraenoic acid from arachidonic acid, the highly efficient formation of 8-hydroxyeicosapentaenoic acid from eicosapentaenoic acid, and the highly efficient formation of 10-hydroxy docosahexaenoic acid from docosahexaenoic acid. Specifically, the present invention provides a polynucleotide that comprises the nucleic acid sequence represented by SEQ ID NO: 1 and 3, or a homolog thereof, and a polypeptide that comprises the amino acid sequence represented by SEQ ID NO: 2 and 4, or a homolog thereof. Also provided is a composition that comprises a membrane protein of an organism belonging to the class Malacostraca and is for carrying out a lipoxygenase reaction.

7 Claims, 4 Drawing Sheets
Specification includes a Sequence Listing.

[FIG.1] Nucleic acid sequence of PK LOX1 (SEQ ID NO: 1)

```
ATGGCGCCAATTAAGGAAAAGAAGTCTTTTAAGCTGACTGCTGCAACAGGGAATCAAGA
TGGCGCTGGTACAGATGCCAATGTGTATGTGACCTTTGAGGATGAAGAAGGTCGTCGGA
CGAAAGAGAAAAAGCTTGATAAGCTTCTGTACAATGATCTGGAGAAGGGCAAAAAGGAC
AAGTATGACATCAATGCACCTGTAGAGTTTGGTGCAGTGAAGAAGTTGCATGTCCACAG
GGATTCAACTGGATTGGGAGACTCCTGGTTCTGTGACTACTTCGAAATTAAAGATTTAC
CCTTCAAAGGCAACAATAATGAGCCCAGCCCTACCAAGAAAGAATACTACTATTTTCCC
ATTCACCGTTGGATCAGCTCCCAGCACCGGTATGAGTTTGACGAGTATGGGACATGTCT
ACCACAGGCAGACCCATGCATAGGTCCACGTAAAGCGGATTTGGAGGCCAAAAAGAGCT
CATACAATTATGTGTACCGTATTGGTGCAATGGCGGCTACTGACACTACGGATGCCTGC
GTTGGTCATTGTGCACAGGTGGAGACCCTTCCTGCAGATGAGAAGTTCTCTGAAGATTA
TTATTGGAACTTTGCAACAGATAAGTTAAAACTCCTGGCAGAAACCAAATGGATGGAGT
GGACAAACCAAACAAAATGGAATAGTCTTTCTGATCTCAGAAGTGTTTACAAAAAGAGT
CTTGGAGAACCTAAGTGCTTAGATGTTTGGCGTGAAGACTGGTGGTTTGGACTACAACG
ACTACAAGGGGTCAACCCAGTTATTATTGAGCTATGTACTCAGATACCTGATAACCTAG
CTGTGACTGACACCACTGTTGAAGGTCTCATGGATGACTTAACTCTCAATGAAGCTTTA
GAAAATAAGAAAATATTTATATGCGACCTAAAGATCATGGATGGGCTATGCTGTAAAGA
AAATCGAGAGCTTGCAGCTCCCTTGGCGTTGTTCTACCTAAATAAAGAAAATAAGCTGT
TGCCCATCGCACTACAGCTAAAACAGGAAAAAGGAGATGATAACCCAGTTTTCACACCT
AAGGATTCTAAGAATACTTGGTTAGTTGCGAAGATGTTTTATAACAATTCTGAAGCTCA
GCACCACCAAGCACTGACACATCTGGGTTACACACATCTCCTCATGGAGGGAGTAGTGG
TCTGCACACACAGAAACCTCTCACCTTCACATCCACTCTTCAAGCTTATGGGCACCGCAT
TTCTTGTTTCTCTTGGCCATTAACTCGCGTGGTCTTGAAAAGTTAGTTTCCGAAGGTGG
ATGGGTTGATTGCTGCATGACACAGGGCCTTTGTGGCATCTTGGATCTAATGAAGCGAG
GATTTGAAGCATGGACATACACAAAGTTTGGCTCGGTTTCTGCAGAGCTTGAAGCCCGT
GGTGTATTAAACAAAGATGTTCTTCCATATTATCCATATAGAGACGATGCTCTACCTCT
ATTTGCTGAAATCAGAAAATATGTCAAAACTATTGTTGAGCACCACTATGATAATGAAG
ATAAGATGAAAGAAGACTGGGAGTTAAAAAGCTGGAGGGAGGAGTTAGCCAAGCAGCGG
AGTGAAAATGGAGTTGGACTTGCTGATATCCCGGGCTCGAAAGAAGATGGTTTCAATAG
TGTGGATGAAGTAGTAGATGTGGTGACAATGATTATTTCAACATGCTCTCTTGGTCATG
CTGCATCAAACTTCCAGCAGTATGAACAGTACGGATATGTGCCAAATTACCCTGGTATT
CTCATGTCTACCTTGCCTAAAGAAAAGAAAGAGTATACAGAAGAAGAAATCATGCAGAT
CCTCCCAGACAAGCGGATGACTTTGGATATCATGGTCATCACAAAGCTACTGTCAACCA
AAGGAACACAAAGTCTCGGGGACTTTGAAATGCAGTATCTGTATGACCCTGTAGGAGTC
CAGGCGGCTAAAGATTTCCGCAAAAACCTTGATCGATTGAGTAAAAAAAATAAACTTGA
AAATGTTGATCGACAATGGGACTTTGATTGGCTTGATCCAGAATTTGTTCCAAATGCCA
TCAGTGTATAA
```

[FIG.2] Amino acid squence of PK LOX1 (SEQ ID NO: 2)

```
MAPIKEKKSFKLTAATGNQDGAGTDANVYVTFEDEEGRRTKEKKLDKLLYNDLEKGKKD
KYDINAPVEFGAVKKLHVHRDSTGLGDSWFCDYFEIKDLPFKGNNNEPSPTKKEYYYFP
IHRWISSQHRYEFDEYGTCLPQADPCIGPRKADLEAKKSSYNYVYRIGAMAATDTTDAC
VGHCAQVETLPADEKFSEDYYWNFATDKLKLLAETKWMEWTNQTKWNSLSDLRSVYKKS
LGEPKCLDVWREDWWFGLQRLQSVNPVIIELCTQIPDNLAVTDTTVEGLMDDLTLNEAL
ENKKIFICDLKIMDGLCCKENRELAAPLALFYLNKENKLLPIALQLKQEKGDDNPVFTP
KDSKNTWLVAKMFYNNSEAQHHQALTHLGYTHLLMEGVVVCTHRNLSPSHPLFKLMAPH
FLFLLAINSRGLEKLVSEGGWVDCCMTQGLCGILDLMKRGFEAWTYTKFGSVSAELEAR
GVLNKDVLPYYPYRDDALPLFAEIRKYVKTIVEHHYDNEDKMKEDWELKSWREELAKQR
SENGVGLADIPGSKEDGFNSVDEVVDVVTMIISTCSLGHAASNFQQYEQYGYVPNYPGI
LMSTLPKEKKEYTEEEIMQILPDKRMTLDIMVITKLLSTKGTQSLGDFEMQYLYDPVGV
QAAKDFRKNLDRLSKKNKLENVDRQWDFDWLDPEFVPNAISV
```

[FIG.3]

Nucleic acid squence of PK LOX 2 (SEQ ID NO: 3)

ATGGTAGCGCTGCGCTGCTTCAAACCAGAGGAAATGCATATTTTTACAATATGTGGACT
TTTTTTGGCGGCAATGGAGGTCTCAAATGCTTATCTATGTAATAACAACTTTTTGGTGA
CTGTGAAGACTGGTTATGGGACAGATGCTGGCTCAAATGCAAGTGTGATATTAGTATTA
GAAGATCAAAATAGAAATGAAATTAGAAATTGGTTAAGTATTCCGAAACAAGATGAAAC
TGGAAATCATAGGATACCTATACCAACGAGTTTTGGAAGAATAGTGACTGTAGAATTAG
CCCTAGATTATAAGCTTGCTCCCGATTGGTATTGTGAGGATATCTTTATTGAAGATCCT
CGACTAAATGACAGATTATATTTTCCAATTGATCGAAGAATTCAAGGTAACCAGTTTTA
TGATTTTCAAAACTATGCCACTTGCCTACCACAATTTGACCAAAATAGTATAAGCAGAA
GATTGACTCTACAAAAGAAGAGAGAAGATTATCAACTATCTTACGACCGTACAGCTGCA
ATGGTTAAAGATCTCCCACAGGATGAAATATTTCATCAGGATTATATTTCTAGCATTAG
AGCAATACAAAAGACGTCTATTGATGACCAGATACCTCTGCTCCAAGCATGGCAGAGTT
CTAACAATATCAGCGCATTTTTTGGAGGAGACTTTTACATGCCACAGAGTATACAGTTT
TGGAAAGAAGATGCATGGTTTGGTGCTCAGCGTGTTCAAGGGATAGTACCAAATATTAT
TGAACTTTGTAAACAAATTCCAGATAAATTAGGAGTGACAGAAGATACCATTAGTGGGC
TTCTAGAAGGCTCTACTCTCCAACAGGCATTAAAGAACAACAAAATATTTATATCCGAC
CTGGAACTCTTAGATGGGATACAGTATAGTGGAGTGTGGAGTGACAATGCAGATCATGC
CGCGCCTATTTCGGTTTTTTATCTCAATAAAATAGATCAATTAATGCCCATCGTCAATTC
AGCTCAGACAACAGAAAGGTCCAAAAAACCCTGTCTATACCCCTAAAGACCCACCAAAT
ACCTGGCTTGTTGCTAAGATATATTATAACAATGCAGAATCCCAGTTCCATCAAATTCT
GGTTCATTTTGGCTATACCCATATGATAATGGATGGCATCGCTACAAGTATGAACCGGC
AACTGTCACCATCACATCCCGTGTTCAAAATCCTGAAGCCGCACTTTCTATATCTTCTG
GCTATTAACAGATTAGGAGAACAAGAATTATTTGTGCCCCAAGGAGTGTTCCCATATTT
TTCTATTGGCTTAGATGGCATGAACCAACTACTGGCAAAGGCAGTTCCACAATTCACCC
TCGCAAGAGCTATTGGATCAGTTGAATCTGACGCCAGGGCTCGTGGAGTTTGGGATAAA
CAGGTTCTCCCGTATTACCCATTTAGAGATGATGCGCACTCTATGTACAACATCATCAA
GAAATATGCCACTAAAGTTATTTATTATTATTATAATACACCAGGAAAAATTATCAATG
ATATGGAGCTGCAGAGGTGGCGTACTGAGCTTGCTAAGCCCAGAGCTCAAGGAGGTGTT
GGTATCCCTGATCTTCCTGGATCTGATACAGCAGGTTTCCGTGACATTAATGAAATTAT
CGATTTGGTAACAACCATTATCACTCATAGTTCAGTTGGTCATGCAGCTGTCAACTTCC
CCATGTATGATACATATGGATATTTCCCAAATTACCCTCCAGATTTAAATGAAGGACCT
CCTCTGCAAAAAATGTTATATACAGAAGATGAGATTATGAGCTTATTCCCTAATGGGAG
CCATGCGTTCAGGGTCAGGGCCACAATAAGGGTCTTATCGTGGCAAGGAACCAATGACT
GTGGGGACTTTGAAAAAATATACCTGTATGACCCAGTCAGTCAGGAAGCTCAAGTTGAA
CTCAGAAAAGATCTTGCTATGTTTAGCAAGGAAGTGATGAACAGAAATAGTAAAAGATT
TATTCCGTATAAATATCTAGACCCAAATTATGTTCCAAATGCAATAAGTATTTAG

[FIG.4]

Amino acid sequence of PK LOX2 (SEQ ID NO: 4)

MVALRCFKPEEMHIPTICGLPLAAMEVSNAYLCNNNFLVTVKTGYGTDAGSNASVILVL
EDQNRNEIRNWLSIPKQDETGNHRIPIPTSFGRIVTVELALDYKLAPDWYCEDIFIEDP
RLNDRLYFPIDRRIQGNQFYDFQNYATCLPQFDQNSISRRLTLQKKREDYQLSYDRTAA
MVKDLPQDEIFHQDYISSIRAIQKTSIDDQIPLLQAWQSSNNISAFFGGDFYMPQSIQF
WKEDAWFGAQRVQGIVPNIIELCKQIPDKLGVTEDTISGLLEGSTLQQALKNNKIFISD
LELLDGIQYSGVWSDNADHAAPISVFYLNKILQLMPIAIQLRQQKGPKNPVYTPKDPPN
TWLVAKIYYNNAESQFHQILVHFGYTHMIMDGIATSMNRQLSPSHPVFKILKPHFLYLL
AINRLGEQELFVPQGVFPYFSIGLDGMNQLLAKAVPQFTLARAIGGVESDARAKGVWDK
QVLPYYPFRDDAHSMYNIIKKYATKVIYYYNTPGKIINDMELQRWRTELAKPRAQGGV
GIPDLPGSDTAGFRDINEIIDLVTTIITHSSVGHAAVNFPMYDTYGYFPNYPPDLNEGP
PLQKMLYTEDEIMSLFPNGSHAFRVRATIRVLSWQGTNDCGDFEKIYLYDPVSQEAQVE
LRKDLAMFSKEVMNRNSKRFIPYKYLDPNYVPNAISI

[FIG.5]
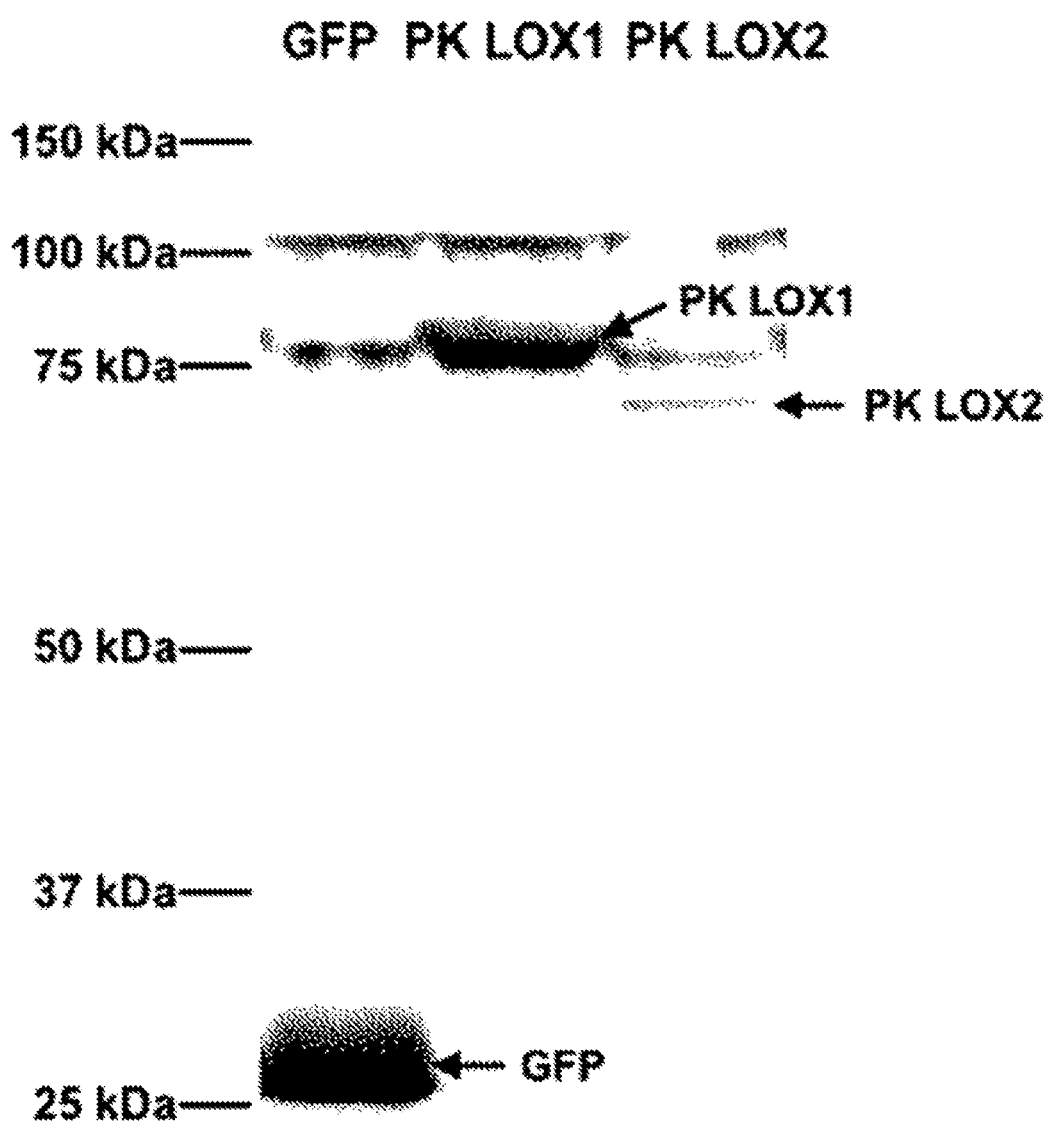

[FIG.6]
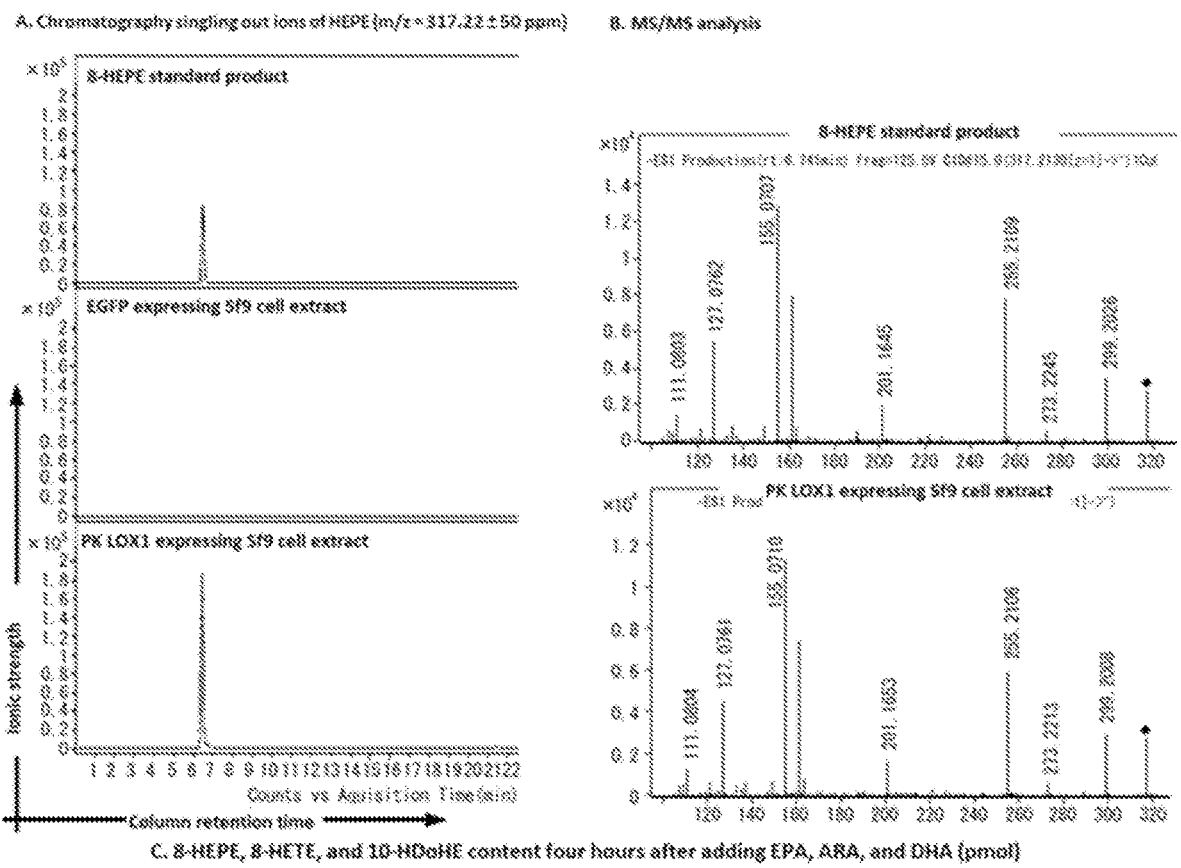
[FIG.7]
| | 8-HEPE |
|---|---|
| EGFP expressing Sf9 cell | Not detected |
| PK LOX2 expressing Sf9 cell | 2 pmol |

OXIDATION OF HIGHLY UNSATURATED FATTY ACIDS WITH NOVEL 8-LIPOXYGENASE DERIVED FROM MALACOSTRACA

STATEMENT REGARDING SEQUENCE LISTING

The Sequence Listing associated with this application is provided in text format in lieu of a paper copy, and is hereby incorporated by reference into the specification. The name of the text file containing the Sequence Listing is 150134_409USPC_SEQUENCE_LISTING.txt. The text file is 33.5 KB, was created on Aug. 26, 2020, and is being submitted electronically via EFS-Web.

TECHNICAL FIELD

The present invention relates to a novel 8-lipoxygenase and a nucleic acid encoding the same, and a method of use thereof. The present invention also relates to a method of oxidizing a highly unsaturated fatty acid using a novel 8-lipoxygenase.

BACKGROUND ART

The physiological function of metabolites of highly unsaturated fatty acids has drawn attention. For example, an 8-hydroxyeicosapentaenoic acid (8-HEPE) is a derivative generated by oxidation (hydroxylation) of carbon at position 8 of an eicosapentaenoic acid (EPA). 8-HEPE is a compound that has a higher peroxisome proliferator-activated receptor (PPAR) activating action than EPA and is expected to have an effect of preventing/improving metabolic diseases such as obesity and diabetes (Non Patent Literature 1).

8-HEPE does not exist in nature at a large quantity. For example, Pacific krill (*Euphausia pacifica*) contains only 10 s of ppm of 8-HEPE (Non Patent Literature 2).

While there are currently efforts to prepare an 8-HEPE concentrated ingredient from Pacific krill for practical application thereof as an ingredient of functional food, the amount of 8-HEPE harvested from Pacific krill is miniscule, as described above. Besides 8-HEPE, Pacific krill contains several ppm of 8-hydroxyeicosatetraenoic acid (8-HETE) produced by introduction of a hydroxyl group to position 8 of an arachidonic acid and 10-hydroxydocosahexaenoic acid (10-HDoHE) produced by introduction of a hydroxyl group to position 10 of an docosahexaenoic acid (DHA). Such derivatives are also expected to be utilized as a novel functional component or pharmaceutical product (Non Patent Literatures 3 and 4).

However, utilization of such derivatives as a novel functional component or pharmaceutical product was challenging due to the low content of these derivatives in Pacific krill.

Information on prior art documents related to the invention of the present application includes the following.

CITATION LIST

Non Patent Literature

[NPL 1] Yamada H et al., Journal of Lipid Research, 55, 895-904, 2014
[NPL 2] Yamada H et al., Scientific Reports, 7, 9944, 2017
[NPL 3] Klawitter J et al., J Lipid Res. 2014 June; 55(6): 1139-49.
[NPL 4] Hashimoto M et al., Biochim Biophys Acta. 2015 February; 1851 (2): 203-9

SUMMARY OF INVENTION

Technical Problem

In this regard, there is a demand for a technology for mass producing 8-HEPE, i.e., technology for enzymatically producing 8-HEPE, for utilization as a novel functional component or pharmaceutical product.

Solution to Problem

After noting that Pacific krill contains, besides 8-HEPE that is a derivative generated by oxidation (hydroxylation) of carbon at position 8 of an eicosapentaenoic acid (EPA), several ppm of 8-hydroxyeicosatetraenoic acid (8-HETE) produced by introduction of a hydroxyl group to position 8 of an arachidonic acid and 10-hydroxydocosahexaenoic acid (10-HDoHE) produced by introduction of a hydroxyl group to position 10 of a docosahexaenoic acid (DHA), and 8-HEPE is in fact produced by incubating a Pacific krill protein and EPA at 20° C., the inventors completed the present invention by isolating/identifying a lipoxygenase gene from Pacific krill and identifying an enzyme that converts an eicosapentaenoic acid (EPA) into an 8-hydroxyeicosapentaenoic acid (8-HEPE).

The inventors employed an approach combining next generation sequencer analysis and bioinformatic analysis for performing de novo RNA sequence analysis on Pacific krill (*Euphausia pacifica*) in order to identify the lipoxygenase gene sequence of Pacific krill, and narrowing down candidate lipoxygenase genetic sequences by Blast search to obtain candidate lipoxygenase genes of Pacific krill, i.e., Pacific krill Lipoxygenase clones 1 and 2. Since it was clone 1 between them that encoded a lipoxygenase domain, clone 1 was named PK LOX1. Since a PK LOX2 clone was considered a partial sequence, full length cDNA sequence analysis was performed by Rapid amplification of cDNA ends (RACE) to obtain a full length cDNA sequence. For PK LOX1 and PK LOX2, proteins were expressed in insect cells to test 70 to 80 kDA protein expression and lipoxygenase activity. In this manner, the technical problem described above was solved by finding an enzyme generating an 8-hydroxyeicosapentaenoic acid (8-HEPE) through oxidation of carbon at position 8 of an eicosapentaenoic acid (EPA), an 8-hydroxyeicosatetraenoic acid (8-HETE) through oxidation of carbon at position 8 of an arachidonic acid (ARA), and a 10-hydroxydocosahexaenoic acid (10-HDoHE) through oxidation of carbon at position 10 of a docosahexaenoic acid (DHA).

A lipoxygenase with the same effect as an 8-lipoxygenase of Pacific krill, which was first identified through the present invention, is present not only in Pacific krill, but also in other organisms belonging to Malacostraca, such as other organisms belonging to Euphausiacea and other organisms belonging to Decapoda. It is expected that such a lipoxygenase can be isolated/prepared as a membrane protein.

For example, the present invention provides the following.
(Item 1)
An 8-lipoxygenase derived from Malacostraca, having activity selected from the group consisting of:
(1) activity to oxidize carbon at position 8 of an arachidonic acid;

(2) activity to oxidize carbon at position 8 of an eicosapentaenoic acid; and
(3) activity to oxidize carbon at position 10 of a docosahexaenoic acid.

(Item 2)

The 8-lipoxygenase of item 1, wherein the 8-lipoxygenase is an 8-lipoxygenase derived from Euphausiacea or an 8-lipoxygenase derived from Decapoda.

(Item 3)

A polypeptide selected from the group consisting of:
(a) a polypeptide comprising the amino acid sequence selected from the group consisting of SEQ ID NO: 2 and SEQ ID NO: 4;
(b) a polypeptide consisting of an amino acid sequence that is at least 90% identical to the amino acid sequence selected from the group consisting of SEQ ID NO: 2 and SEQ ID NO: 4;
(c) a polypeptide consisting of an amino acid sequence comprising one or several mutations, substitutions, insertions, or deletions in the amino acid sequence selected from the group consisting of SEQ ID NO: 2 and SEQ ID NO: 4;
(d) a polypeptide encoded by a nucleic acid comprising the nucleic acid sequence selected from the group consisting of SEQ ID NO: 1 and SEQ ID NO: 3;
(e) a polypeptide encoded by a nucleic acid that hybridizes with a complementary strand of a nucleic acid comprising the nucleic acid sequence selected from the group consisting of SEQ ID NO: 1 and SEQ ID NO: 3 under a high stringency condition;
(f) a polypeptide encoded by a nucleic acid comprising a sequence that is at least 90% identical to the nucleic acid sequence selected from the group consisting of SEQ ID NO: 1 and SEQ ID NO: 3; and
(g) a polypeptide encoded by a nucleic acid having a nucleic acid sequence comprising one or several mutations, substitutions, insertions, or deletions in the nucleic acid sequence selected from the group consisting of SEQ ID NO: 1 and SEQ ID NO: 3;
wherein the polypeptide has activity selected from the group consisting of:
(1) activity to oxidize carbon at position 8 of an arachidonic acid;
(2) activity to oxidize carbon at position 8 of an eicosapentaenoic acid; and
(3) activity to oxidize carbon at position 10 of a docosahexaenoic acid.

(Item 4)

The polypeptide of item 3, selected from the group consisting of:
(a) a polypeptide comprising the amino acid sequence selected from the group consisting of SEQ ID NO: 2 and SEQ ID NO: 4; and
(d) a polypeptide encoded by a nucleic acid comprising the nucleic acid sequence selected from the group consisting of SEQ ID NO: 1 and SEQ ID NO: 3.

(Item 5)

A method of generating an oxide by reacting the polypeptide of any one of items 1 to 4 with a highly unsaturated fatty acid or a derivative of a highly unsaturated fatty acid.

(Item 6)

The method of item 5, wherein:
the highly unsaturated fatty acid is an arachidonic acid, and the oxide is an 8-hydroxyeicosatetraenoic acid;
the highly unsaturated fatty acid is an eicosapentaenoic acid, and the oxide is an 8-hydroxyeicosapentaenoic acid;
the highly unsaturated fatty acid is a docosahexaenoic acid, and the oxide is a 10-hydroxydocosahexaenoic acid; or
the highly unsaturated fatty acid is a docosapentaenoic acid, and the oxide is a 10-hydroxydocosapentaenoic acid.

(Item 7)

A composition for generating an oxide of a highly unsaturated fatty acid or a derivative of a highly unsaturated fatty acid from a highly unsaturated fatty acid or a derivative of a highly unsaturated fatty acid, comprising the polypeptide of any one of items 1 to 4.

(Item 8)

The composition of item 7, wherein
the highly unsaturated fatty acid is an arachidonic acid, and the oxide is an 8-hydroxyeicosatetraenoic acid;
the highly unsaturated fatty acid is an eicosapentaenoic acid, and the oxide is an 8-hydroxyeicosapentaenoic acid; or
the highly unsaturated fatty acid is a docosahexaenoic acid, and the oxide is a 10-hydroxydocosahexaenoic acid.

(Item 9)

A nucleic acid encoding an 8-lipoxygenase derived from Malacostraca, having activity selected from the group consisting of:
(1) activity to oxidize carbon at position 8 of an arachidonic acid;
(2) activity to oxidize carbon at position 8 of an eicosapentaenoic acid; and
(3) activity to oxidize carbon at position 10 of a docosahexaenoic acid.

(Item 10)

The nucleic acid of item 9, wherein the 8-lipoxygenase is an 8-lipoxygenase derived from Euphausiacea or an 8-lipoxygenase derived from Decapoda.

(Item 11)

A nucleic acid selected from the group consisting of:
(h) a nucleic acid comprising the nucleic acid sequence selected from the group consisting of SEQ ID NO: 1 and SEQ ID NO: 3;
(i) a nucleic acid that hybridizes with a complementary strand of a nucleic acid comprising the nucleic acid sequence selected from the group consisting of SEQ ID NO: 1 and SEQ ID NO: 3 under a high stringency condition;
(j) a nucleic acid comprising a sequence that is at least 90% identical to the nucleic acid sequence selected from the group consisting of SEQ ID NO: 1 and SEQ ID NO: 3;
(k) a nucleic acid having a nucleic acid sequence comprising one or several mutations, substitutions, insertions, or deletions in the nucleic acid sequence selected from the group consisting of SEQ ID NO: 1 and SEQ ID NO: 3;
(l) a nucleic acid encoding a polypeptide comprising the amino acid sequence selected from the group consisting of SEQ ID NO: 2 and SEQ ID NO: 4;
(m) a nucleic acid encoding a polypeptide consisting of an amino acid sequence that is at least 90% identical to the amino acid sequence selected from the group consisting of SEQ ID NO: 2 and SEQ ID NO: 4; and
(n) a nucleic acid encoding a polypeptide consisting of an amino acid sequence comprising one or several mutations, substitutions, insertions, or deletions in the amino acid sequence selected from the group consisting of SEQ ID NO: 2 and SEQ ID NO: 4;
wherein the nucleic acid encodes a polypeptide having activity selected from the group consisting of:

(1) activity to oxidize carbon at position 8 of an arachidonic acid;
(2) activity to oxidize carbon at position 8 of an eicosapentaenoic acid; and
(3) activity to oxidize carbon at position 10 of a docosahexaenoic acid.

(Item 12)

The nucleic acid of item 11, selected from the group consisting of:
(h) a nucleic acid comprising the nucleic acid sequence selected from the group consisting of SEQ ID NO: 1 and SEQ ID NO: 3; and
(l) a nucleic acid encoding a polypeptide comprising the amino acid sequence selected from the group consisting of SEQ ID NO: 2 and SEQ ID NO: 4.

(Item 13)

A recombinant vector comprising the nucleic acid of item 11 or 12.

(Item 14)

A transformant comprising the recombinant vector of item 13.

(Item 15)

A method of manufacturing an 8-lipoxygenase, comprising:
culturing the transformant of item 14;
generating and accumulating the 8-lipoxygenase of any one of items 1 to 4 in a culture; and
retrieving the generated and accumulated 8-lipoxygenase.

(Item 16)

A composition for performing a lipoxygenase reaction, comprising a membrane protein of an organism belonging to Malacostraca.

(Item 17)

The composition of item 16, wherein the membrane protein is a membrane protein of an organism belonging to Euphausiacea or a membrane protein of an organism belonging to Decapoda.

(Item 18)

The composition of item 16, wherein the membrane protein is a membrane protein of Pacific krill.

(Item 19)

The composition of any one of items 16 to 18 for generating an oxide of a highly unsaturated fatty acid or a derivative of a highly unsaturated fatty acid from a highly unsaturated fatty acid or a derivative of a highly unsaturated fatty acid.

(Item 20)

The composition of item 19, wherein
the highly unsaturated fatty acid is an arachidonic acid, and the oxide is an 8-hydroxyeicosatetraenoic acid;
the highly unsaturated fatty acid is an eicosapentaenoic acid, and the oxide is an 8-hydroxyeicosapentaenoic acid; or
the highly unsaturated fatty acid is a docosahexaenoic acid, and the oxide is a 10-hydroxydocosahexaenoic acid.

A polynucleotide having a nucleic acid sequence homologous to SEQ ID NO: 1 or SEQ ID NO: 3, or a polypeptide having an amino acid sequence homologous to SEQ ID NO: 2 or SEQ ID NO: 4 can be used in the present invention. A polypeptide isolated from a cell belonging to *Euphausia*, having activity selected from the group consisting of: (1) activity to oxidize carbon at position 8 of an arachidonic acid; (2) activity to oxidize carbon at position 8 of an eicosapentaenoic acid; and (3) activity to oxidize carbon at position 10 of a docosahexaenoic acid, or a polynucleotide encoding such a polynucleotide can also be used in the present invention.

Advantageous Effects of Invention

A lipoxygenase (8-lipoxygenase) provided by the present invention enables highly efficient generation of an 8-hydroxyeicosatetraenoic acid from an arachidonic acid, highly efficient generation of an 8-hydroxyeicosapentaenoic acid from an eicosapentaenoic acid, and highly efficient generation of a 10-hydroxydocosahexaenoic acid from a docosahexaenoic acid.

BRIEF DESCRIPTION OF DRAWINGS

FIG. 1 shows the nucleic acid sequence (SEQ ID NO: 1) of a lipoxygenase gene (PK LOX1) isolated from *Euphausia pacifica*.

FIG. 2 shows the amino acid sequence (SEQ ID NO: 2) of a lipoxygenase (PK LOX1) isolated from *Euphausia pacifica*.

FIG. 3 shows the nucleic acid sequence (SEQ ID NO: 3) of a lipoxygenase gene (PK LOX2) isolated from *Euphausia pacifica*.

FIG. 4 shows the amino acid sequence (SEQ ID NO: 4) of a lipoxygenase (PK LOX2) isolated from *Euphausia pacifica*.

FIG. 5 shows results of expressing the PK LOX1 protein and PK LOX2 protein of the invention tagged with histidine using insect cells, separating the proteins by SDS PAGE, and detecting the proteins using an anti-histidine antibody.

FIG. 6 is a result showing conversion of an eicosapentaenoic acid into 8-HEPE by the PK LOX1 of the invention.

FIG. 7 is a result showing conversion of an eicosapentaenoic acid into 8-HEPE by the PK LOX2 of the invention.

DESCRIPTION OF EMBODIMENTS

The present invention is described hereinafter. Throughout the entire specification, a singular expression should be understood as encompassing the concept thereof in the plural form, unless specifically noted otherwise. The terms used herein should also be understood as being used in the meaning that is commonly used in the art, unless specifically noted otherwise. Thus, unless defined otherwise, all terminologies and scientific technical terms that are used herein have the same meaning as the general understanding of those skilled in the art to which the present invention pertains. In case of a contradiction, the present specification (including the definitions) takes precedence.

Definitions of the Terms

The definitions of the terms particularly used herein are listed hereinafter.

The term "unsaturated fatty acid" as used herein refers to a fatty acid with one or more unsaturated carbon bonds. An unsaturated carbon bond is an unsaturated bond between carbons in a carbon molecule chain, i.e., carbon double bond or triple bond. An unsaturated fatty acid found in nature has one or more double bonds. A replacement of a saturated fatty acid in fat with an unsaturated fatty acid results in a change in the properties of fat, such as the melting point or fluidity.

The term "highly unsaturated fatty acid" as used herein refers to an unsaturated fatty acid with 16 or more carbons and two or more double bonds within a molecule. Examples thereof include, but are not limited to, docosahexaenoic acid (C22:6, DHA), eicosapentaenoic acid (C20:5, EPA), arachidonic acid (C20:4, AA), docosapentaenoic acid (C22:5, DPA), stearidonic acid (C18:4), linolenic acid (C18:3), linoleic acid (C18:2), tetracosahexaenoic acid (C24:6), eicosatetraenoic acid (C20:4, ETA), eicosatrienoic acid (C20:3), and the like. A highly unsaturated fatty acid can be a free fatty acid. A derivative of a highly unsaturated fatty acid obtained by the acquisition method of the invention refers to a free or non-free fatty acid. Examples thereof include, but are not limited to, highly unsaturated fatty acids, phospholipids that bind to a highly unsaturated fatty acid, triglycerides that bind to a highly unsaturated fatty acid, highly unsaturated fatty acid's esteric derivatives such as methyl ester and ethyl ester, amidic derivatives such as ethylamide and methylamide, fatty alcohol derivatives, triglycerides, diglycerides, monoglycerides, and the like. An unsaturated fatty acid derivative such as a highly unsaturated fatty acid derivative can also be used as a substrate. Examples of derivatives of highly unsaturated fatty acids include, but are not limited to, ethyl esters of a highly unsaturated fatty acid, triglycerides comprising a highly unsaturated fatty acid, diglycerides comprising a highly unsaturated fatty acid, monoglycerides comprising a highly unsaturated fatty acid, phospholipids comprising a highly unsaturated fatty acid, lysophospholipids comprising a highly unsaturated fatty acid, sphingolipids comprising a highly unsaturated fatty acid, glycolipids comprising a highly unsaturated fatty acid, and amidic derivatives of a highly unsaturated fatty acid (e.g., fatty acid amide such as ethanolamide of a highly unsaturated fatty acid). Derivatives of a highly unsaturated fatty acid also encompass esters of the highly unsaturated fatty acid. An unsaturated fatty acid ester (e.g., unsaturated fatty acid ethyl ester), especially a highly unsaturated fatty acid ester (e.g., highly unsaturated fatty acid ethyl ester) can also be used as a substrate for an enzymatic reaction.

"Oxidation" of an unsaturated fatty acid as used herein refers to a reaction that oxidizes a functional group (e.g., carbon) of an unsaturated fatty acid, especially a reaction in which a hydrogen atom is converted into a hydroxyl group.

As used herein, "kit" refers to a product comprising a plurality of containers and an instruction manual from the manufacturer, wherein each container comprises the nucleic acid and/or polypeptide of the invention.

"Polynucleotide", "nucleic acid", or "nucleic acid molecule" can refer to a phosphoester polymer form ribonucleotide (adenosine, guanosine, uridine, or cytidine; "RNA molecule") or deoxyribonucleotide (deoxyadenosine, deoxyguanosine, deoxythymidine, or deoxycytidine; "DNA molecule") in a single stranded form, double stranded form, or other forms, or any phosphoester analog thereof (e.g., phosphorothioate or thioester). A "polynucleotide", "nucleic acid", or "nucleic acid molecule" possesses "base sequence" information.

"Polynucleotide sequence", "base sequence", "nucleic acid sequence", or "nucleotide sequence" refers to a sequence of a series of nucleotide bases (also known as "nucleosides") in a nucleic acid (e.g., DNA or RNA), which is a sequence of two or more nucleotides in any strand or a complementary strand thereof. Preferred nucleic acids of the invention include the nucleic acids set forth in SEQ ID NO: 1 and/or SEQ ID NO: 3, and complementary strands, variants, and fragments thereof.

"Complementary strand" refers to a nucleotide strand that can form a base pair with a nucleic acid sequence. For example, each of the strands of a double stranded DNA has a base sequence that is complementary to each other. From the viewpoint of one of the strands, the other strand is a complementary strand.

"Coding sequence" or a sequence "encoding" an expression product (e.g., RNA, polypeptide, protein, or enzyme) is a nucleotide sequence that induces production of the product when expressed.

"Protein", "peptide", or "polypeptide" comprises a contiguous string of two or more amino acids. Preferred peptides of the invention include the peptides set forth in SEQ ID NO: 2 and/or SEQ ID NO: 4, and variants and fragments thereof.

"Protein sequence", "peptide sequence", "polypeptide sequence", or "amino acid sequence" refers to a sequence of a series of two or more amino acids in a protein, peptide, or polypeptide.

Identity of sequences (nucleic acid sequences, amino acid sequences, or the like) as used herein refers to the degree of identity of sequences (individual nucleic acid, amino acid, or the like) with respect to one another of two or more comparable sequences. Thus, higher homology of two genes results in higher identity or similarity of the sequences thereof. Whether two genes have high identity can be found by direct comparison of sequences, or by a hybridization method under stringent conditions for nucleic acids. When two genetic sequences are directly compared, the genes are homologous if the DNA sequences are typically at least 50% identical, preferably at least 70% identical, more preferably at least 80%, 90%, 95%, 96%, 97%, 98%, or 99% identical between the genetic sequences. Alternatively, compared amino acid sequences are homologous if the amino acid sequences are typically at least 50% identical, preferably at least 70% identical, more preferably at least 80%, 90%, 95%, 96%, 97%, 98%, or 99% identical. As used herein, "similarity" of genes (e.g., nucleic acid sequences, amino acid sequences, or the like) refers to the degree of identity of two or more genetic sequences to one another when a conservative substitution is considered positive (identical) with regard to the homology described above. Therefore, if there is a conservative substitution, homology and similarity differ in accordance with the presence of the conservative substitution. If there is no conservative substitution, homology and similarity indicate the same numerical value.

Similarity, identity, and homology of amino acid sequences and base sequences are compared and computed using a sequence analysis tool BLAST with default parameters. Alternatively, identity of amino acid sequences and base sequences can be computed by aligning two sequences to be compared and calculating the ratio of identical residues to the entire sequence.

As used herein, "fragment" refers to a polypeptide or a polynucleotide with a sequence length of 1 to n−1 with respect to a full length polypeptide or polynucleotide (with a length of n). The length of a fragment can be appropriately changed depending on the objective. Examples of the lower limit of the length include, for polypeptides, 3, 4, 5, 6, 7, 8, 9, 10, 15, 20, 25, 30, 40, 50, or more amino acids. Lengths represented by an integer that is not specifically listed herein (e.g., 11) can also be suitable as the lower limit. Examples thereof include, for polynucleotides, 5, 6, 7, 8, 9, 10, 15, 20, 25, 30, 40, 50, 75, 100, or more nucleotides. Lengths represented by an integer that is not specifically listed herein (e.g., 11) can also be suitable as the lower limit. The lengths of polypeptides and polynucleotides herein can be represented by the number of amino acids and nucleic acids, respectively, as described above, but the aforementioned number is not absolute. As long as the function is the same, the numbers described above as the upper limit or lower limit are intended to include numbers that are several numbers above or below (or, for example, ±10%). To express such an intent, the number can be expressed herein by appending "about" in front of the number. However, it is understood that the presence/absence of "about" does not affect the interpretation of the numerical value. The length of a fragment that is useful herein can be determined by whether at least one of the functions of the full length protein, which is the baseline of the fragment, is retained.

As used herein, an "isolated" biological factor (e.g., nucleic acid, protein, or the like) refers to a biological factor that is substantially purified or separated from other naturally-occurring biological factors (e.g., for nucleic acids, factors other than nucleic acids and nucleic acids comprising a nucleic acid sequence other than the nucleic acid of interest; for proteins, factors other than proteins and proteins comprising an amino acid sequence other than the protein of interest) within a cell of an organism in which the biological factors of interest are present in nature. "Isolated" nucleic acids and proteins include nucleic acids and proteins purified by a standard purification method. Therefore, isolated nucleic acids and proteins include chemically synthesized nucleic acids and proteins.

As used herein, a "purified" biological factor (e.g., nucleic acid, protein, or the like) refers to a biological factor with at least some of the factors naturally accompanying the biological factor removed. Thus, the purity of a biological factor in a purified biological factor is normally higher than the purity in a normal state of the biological factor (i.e., concentrated).

The term "purified" and "isolated" as used herein refers to the presence of the same type of biological factor at preferably at least 75% by weight, more preferably at least 85% by weight, still more preferably at least 95% by weight, and most preferably at least 98% by weight.

As used herein, "polynucleotide that hybridizes under a stringent condition" implies a well-known condition that is commonly used in the art. Such a polynucleotide can be obtained by using colony hybridization, plaque hybridization, Southern blot hybridization, or the like while using a polynucleotide selected from the polynucleotides of the invention as a probe. Specifically, such a polynucleotide refers to a polynucleotide which can be identified using a filter with an immobilized DNA derived from a colony or a plaque for hybridization at 65° C. in the presence of 0.7 to 1.0 M NaCl, and then using an SSC (saline-sodium citrate) solution with a 0.1 to 2× concentration (composition of an SSC solution with 1× concentration is 150 mM sodium chloride and 15 mM sodium citrate) to wash the filter under 65° C. conditions. Hybridization can be performed in accordance with the method described in experimental publications such as Molecular Cloning 2nd ed., Current Protocols in Molecular Biology, Supplement 1 to 38, DNA Cloning 1: Core Techniques, A Practical Approach, Second Edition, Oxford University Press (1995). In this regard, a sequence comprising only an A sequence or only a T sequence is preferably excluded from a sequence that hybridizes under a stringent condition. "Hybridizable polynucleotide" refers to a polynucleotide that can hybridize with another polynucleotide under the hybridization conditions described above. Specific examples of hybridizable polynucleotides include polynucleotides having at least 60% homology, preferably 80% or greater homology, and more preferably 95% or greater homology to a base sequence of DNA encoding a polypeptide having the amino acid sequence specifically shown in the present invention.

As used herein, "high stringency condition" refers to a condition designed to enable hybridization of a DNA strand with high complementarity in a nucleic acid sequence and exclude hybridization of DNA with a significant number of mismatches. The stringency of hybridization is mainly determined by conditions of temperature, ionic strength, and denaturing agent such as formamide. While such "high stringency conditions" for hybridization and washing are not limited, representative examples thereof include: (1) 0.0015 M sodium chloride, 0.0015 M sodium citrate, 65 to 68° C., (2) 0.015 M sodium chloride, 0.0015 M sodium citrate, and 50% formamide, 42° C., (3) 0.3 M sodium chloride, 0.03 M sodium citrate, 0.1% SDS, 65 to 68° C., (4) 0.15 M sodium chloride, 0.015 M sodium citrate, 0.1% SDS, 65 to 68° C., or (5) 0.03 M sodium chloride, 0.003 M sodium citrate, 0.1% SDS, 65 to 68° C. For such high stringency conditions, see Sambrook et al., Molecular Cloning: A Laboratory Manual, Second Edition, Cold Spring Harbor Laboratory (Cold Spring Harbor, N.Y. 1989); and Anderson et al., Nucleic Acid Hybridization: a Practical approach, IV, IRL Press Limited (Oxford, England). Limited, Oxford, England. Optionally, a more stringent condition (e.g., higher temperature, lower ionic strength, more formamide, or another denaturing agent) can be used. Another agent can be included in a hybridization buffer or washing buffer in order to reduce non-specific hybridization and/or background hybridization. Examples of such another agent include 0.1% bovine serum albumin, 0.1% polyvinylpyrrolidone, 0.1% sodium pyrophosphate, 0.1% sodium dodecyl sulfate (Na-DodSO$_4$ or SDS), Ficoll, Denhardt solution, ultrasound treated salmon semen DNA (or another non-complementary DNA), and dextran sulfate, but other suitable agents can also be used. The concentration and type of additives can be changed without substantially affecting the stringency of hybridization conditions. A hybridization experiment is generally performed at a pH of 6.8 to 7.4. Meanwhile, the hybridization rate is mostly independent of pH under typical ionic strength conditions. See Anderson et al., Nucleic Acid Hybridization: a Practical Approach, Chapter 4, IRL Press Limited (Oxford, England).

Examples of factors that affect the stability of a DNA double strand include base composition, length, and degree of base pair mismatch. Hybridization conditions can be adjusted by those skilled in the art, which allows these variables to be applied and DNAs with varying sequence relevance to form a hybrid. The melting temperature of completely matching DNA double strands can be roughly estimated by the following equation.

$$T_m(° C.)=81.5+16.6(\log [Na^+])+0.41(\% G+C)-600/N-0.72(\% \text{ formamide})$$

wherein N is the length of the double strand formed, [Na$^+$] is the molar concentration of sodium ions in a hybridization solution or washing solution, and % G+C is the percentage of (guanine+cytosine) bases in the hybrid. For non-completely matching hybrids, the melting temperature decreases by about 1° C. for each 1% mismatch.

As used herein, "moderate stringency condition" refers to a condition under which a DNA double strand having base pair mismatches at a higher degree than those that can occur under a "high stringency condition" can be formed. Representative examples of "moderate stringency condition" include 0.015 M sodium chloride, 0.0015 M sodium citrate, 50 to 65° C. and 0.015 M sodium chloride, 0.0015 M sodium citrate, 20% formamide, 37 to 50° C. For example, a "moderate stringency condition" of 50° C. allows for about 21% mismatch in 0.015 M sodium ions.

A suitable rough estimation of the melting temperature in 1M NaCl for an oligonucleotide probe of up to about 20 nucleotides is provided by Tm=(2° C. for each A-T base pair)+(4° C. for each G-C base pair). The sodium ion concentration in 6× sodium citrate (SSC) is 1 M (see Suggs et al., Developmental Biology Using Purified Genes, p. 683, Brown and Fox (Ed.) (1981)).

A natural nucleic acid encoding a protein such as a polypeptide with the amino acid sequence of SEQ ID NO: 2 and/or SEQ ID NO: 4 or a variant or fragment thereof is readily separated from a cDNA library with a PCR primer and a hybridization probe comprising a part of the nucleic acid sequence of SEQ ID NO: 1 and/or SEQ ID NO: 3 or a variant thereof. A nucleic acid encoding polypeptide with the amino acid sequence of SEQ ID NO: 2 and/or SEQ ID NO: 4 or a variant or fragment thereof can be hybridized with the sequences set forth in SEQ ID NO: 1 and/or 3 or a part thereof, under low stringency conditions that are defined by a hybridization buffer essentially containing 1% bovine serum albumin (BSA); 500 mM sodium phosphate ($Na_2HPO_4/NaH_2PO_4$); 1 mM EDTA; and 7% SDS at a temperature of 42° C., and a washing buffer essentially containing 2×SSC (600 mM NaCl; 60 mM sodium citrate); and 0.1% SDS at 50° C., more preferably under low stringency conditions that are defined by a hybridization buffer essentially containing 1% bovine serum albumin (BSA); 500 mM sodium phosphate ($Na_2HPO_4/NaH_2PO_4$); 15% formamide; 1 mM EDTA; and 7% SDS at a temperature of 50° C., and a washing buffer essentially containing 1×SSC (300 mM NaCl; 30 mM sodium citrate); and 1% SDS at 50° C., and most preferably under low stringency conditions that are defined by a hybridization buffer essentially containing 1% bovine serum albumin (BSA); 200 mM sodium phosphate ($NaPO_4$); 15% formamide; 1 mM EDTA; and 7% SDS at a temperature of 50° C., and a washing buffer essentially containing 0.5×SSC (150 mM NaCl; 15 mM sodium citrate); and 0.1% SDS at 65° C.

The percentage of "identity", "homology", and "similarity" of sequences (amino acid, nucleic acid, or the like) herein is found by comparing two sequences aligned in the optimal state in a comparison window. In this regard, the portion of a polynucleotide sequence or a polypeptide sequence within the comparison window may comprise an addition or deletion (i.e., gap) when compared to a reference sequence for the optimal alignment of the two sequences (while a gap may occur if another sequence has an addition, the reference sequence is assumed to have no addition or deletion in this case). The percentage of identity is computed by finding the number of matched positions from finding the number of positions at which the same nucleic acid base or amino acid residue is found in both sequences, dividing the number of matched positions by the total number of positions within the comparison window, and multiplying the obtained result by 100. When used in search, homology is evaluated using a suitable algorithm or program from various sequence comparison algorithms and programs that are well known in the art. Examples of such algorithms and programs include, but are not limited in any manner to, TBLASTN, BLASTP, FASTA, TFASTA, and CLUSTALW (Pearson and Lipman, 1988, Proc. Natl. Acad. Sci. USA 85(8): 2444-2448, Altschul et al., 1990, J. Mol. Biol. 215(3): 403-410, Thompson et al., 1994, Nucleic Acids Res. 22(2): 4673-4680, Higgins et al., 1996, Methods Enzymol. 266: 383-402, Altschul et al., 1990, J. Mol. Biol. 215(3): 403-410, Altschul et al., 1993, Nature Genetics 3: 266-272). In a particularly preferred embodiment, homology of protein and nucleic acid sequences is evaluated by using Basic Local Alignment Search Tool (BLAST) that is well known in the art (e.g., Karlin and Altschul, 1990, Proc. Natl. Acad. Sci. USA 87: 2267-2268, Altschul et al., 1990, J. Mol. Biol. 215: 403-410, Altschul et al., 1993, Nature Genetics 3: 266-272, Altschul et al., 1997, Nuc. Acids Res. 25: 3389-3402). In particular, comparison or search can be accomplished by performing the following operations using five dedicated BLAST programs.

(1) Comparison of an amino acid query sequence against a protein sequence database using BLASTP and BLAST3;

(2) Comparison of a nucleotide query sequence against a nucleotide sequence database using BLASTN;

(3) Comparison of a conceptual translation product obtained by converting a nucleotide query sequence (both strands) in six reading frames against a protein sequence database using BLASTX;

(4) Comparison of a protein query sequence against a nucleotide sequence database converted in all six reading frames (both strands) using TBLASTN; and (5) Comparison of a nucleotide query sequence converted in six reading frames against a nucleotide sequence database converted in six reading frames using TBLASTX.

BLAST programs identify homologous sequences by identifying similar segments known as a "high score segment pair" between an amino acid or nucleic acid query sequence and preferably a test sequence obtained from a protein sequence or nucleic acid sequence database. Many high score segment pairs are preferably identified (i.e., aligned) by a scoring matrix that is well known in the art. The BLOSUM 62 matrix (Gonnet et al., 1992, Science 256: 1443-1445, Henikoff and Henikoff, 1993, Proteins 17: 49-61) is preferably used as the scoring matrix. While not as preferable as this matrix, a PAM or PAM 250 matrix can also be used (see, for example, Schwartz and Dayhoff, eds., 1978, Matrices for Detecting Distance Relationships: Atlas of Protein Sequence and Structure, Washington: National Biomedical Research Foundation). BLAST programs evaluate the statistical significance of all identified high score segment pairs and preferably select a segment satisfying a threshold level for significance specified independently by a user such as a homology percentage unique to a user. It is preferable to evaluate the statistical significance of high score segment pairs using the equation of Karlin that finds statistical significance (see Karlin and Altschul, 1990, Proc. Natl. Acad. Sci. USA 87: 2267-2268).

"Primer" as used herein refers to a substance required for initiating a reaction of a macromolecular compound to be synthesized in an enzymatic reaction for synthesizing a macromolecule. A nucleic acid molecule (DNA, RNA, or the like) that is complementary to a part of a sequence of a macromolecular compound to be synthesized can be used in a reaction for synthesizing a nucleic acid molecule.

Examples of nucleic acid molecules generally used as a primer include those with a nucleic acid sequence that is complementary to a nucleic acid sequence of a gene of interest, with a length of at least 8 contiguous nucleotides. Such a nucleic acid sequence can be a nucleic acid sequence with a length of preferably at least 9 contiguous nucleotides, more preferably 10 contiguous nucleotides, still more preferably 11 contiguous nucleotides, 12 contiguous nucleotides, 13 contiguous nucleotides, 14 contiguous nucleotides, 15 contiguous nucleotides, 16 contiguous nucleotides, 17 contiguous nucleotides, 18 contiguous nucleotides, 19 contiguous nucleotides, 20 contiguous nucleotides, 25 contiguous nucleotides, 30 contiguous nucleotides, 40 contiguous nucleotides, or 50 contiguous nucleotides. A nucleic acid sequence used as a primer comprises a nucleic acid sequence that is at least 70% homologous, more preferably at least 80% homologous, still more preferably 90% homologous, and most preferably 95% homologous to the sequence described above. Although a sequence that is suitable as a primer can vary depending on the properties of the sequence intended to be synthesized (amplified), those skilled in the art can design a primer appropriately in accordance with the intended sequence. Design of such a primer is well known in the art. A primer can be designed manually or by using a computer program (e.g., LASERGENE, PrimerSelect, DNAStar).

As used herein, "substitution, addition, or deletion" of a polypeptide or polynucleotide refers to substituting, adding, or removing an amino acid or a replacement thereof or a nucleotide or a replacement thereof in the original polypeptide or polynucleotide, respectively. Technologies for such a substitution, addition, or deletion are well known in the art. Examples of such technologies include site specific mutagenesis technologies. The number of substitutions, additions, or deletions can be any number that is one or greater. Such a number can be increased, as long as the function of interest is retained in a variant with the substitutions, additions, or deletions. Such a number can be, for example, 1, 2, 3, 4, 5, 6, 7, 8, 9, or several, preferably 20% or less or 10% or less of the entire length, 100 or less, 50 or less, 25 or less, or the like.

The molecular biological methodology, biochemical methodology, and microbiological methodology used herein are well known and conventionally used in the art, which are described, for example, in Sambrook J. et al. (1989). Molecular Cloning: A Laboratory Manual, Cold Spring Harbor and 3rd Ed. thereof (2001); Ausubel, F. M. (1987). Current Protocols in Molecular Biology, Greene Pub. Associates and Wiley-Interscience; Ausubel, F. M. (1989). Short Protocols in Molecular Biology: A Compendium of Methods from Current Protocols in Molecular Biology, Greene Pub. Associat ES and Wiley-Interscience; Innis, M. A. (1990). PCR Protocols: A Guide to Methods and Applications, Academic Press; Ausubel, F. M. (1992). Short Protocols in Molecular Biology: A Compendium of Methods from Current Protocols in Molecular Biology, Greene Pub. Associates; Ausubel, F. M. (1995). Short Protocols in Molecular Biology: A Compendium of Methods from Current Protocols in Molecular Biology, Greene Pub. Associates; Innis, M. A. et al. (1995). PCR Strategies, Academic Press; Ausubel, F. M. (1999). Short Protocols in Molecular Biology: A Compendium of Methods from Current Protocols in Molecular Biology, Wiley, and annual updates; Sninsky, J. J. et al. (1999). PCR Applications: Protocols for Functional Genomics, Academic Press, Bessatsu Jikken Igaku [*Experimental Medicine, Supplemental Volume*], "Idenshi Donyu & Hatsugen Kaiseki Jikken Ho" [*Experimental Methods for Gene Transfer & Expression Analysis*], Yodosha, 1997, or the like. Relevant portions thereof (which may be the entire document) are incorporated herein by reference.

DNA synthesis techniques and nucleic acid chemistry for making an artificially synthesized gene are described in, for example, Gait, M. J. (1985). Oligonucleotide Synthesis: A Practical Approach, IRL Press; Gait, M. J. (1990). Oligonucleotide Synthesis: A Practical Approach, IRL Press; Eckstein, F. (1991). Oligonucleotides and Analogues: A Practical Approach, IRL Press; Adams, R. L. et al. (1992). The Biochemistry of the Nucleic Acids, Chapman & Hall; Shabarova, Z. et al. (1994). Advanced Organic Chemistry of Nucleic Acids, Weinheim; Blackburn, G. M. et al. (1996). Nucleic Acids in Chemistry and Biology, Oxford University Press; Hermanson, G. T. (1996). Bioconjugate Techniques, Academic Press, and the like, the relevant portions of which are incorporated herein by reference.

Any suitable method including a molecular biological measurement method such as radiation method, fluorescence method, Northern blotting, dot blotting, or PCR can be used to evaluate the presence of a nucleic acid herein.

The terms "express" and "expression" refer to enabling or inducing information in a gene, RNA sequence, or DNA sequence to be revealed (e.g., protein is generated by activating a cellular function involved with transcription and translation of a corresponding gene). A DNA sequence is expressed in or by a cell to form an "expression product" (e.g., RNA (such as mRNA) or protein). The expression product itself can also be referred to as being "expressed" by the cell.

The term "transformation" refers to introduction of a nucleic acid into a cell. The introduced gene or sequence can be referred to as a "clone". A host cell accepting the introduced DNA or RNA is "transformed", and is a "transformant" or "clone". A DNA or RNA introduced into a host cell can be derived from any source. Such a DNA or RNA can be derived from a cell of the same or different genus or species as the host cell.

The term "vector" encompasses a medium (e.g., plasmid) with which a DNA sequence or RNA sequence can be introduced into a host cell to transform a host and optionally promote expression and/or replication of the introduced sequence.

Examples of vectors that can be used in the present invention include plasmids, viruses, bacteriophages, integratable DNA fragments, and other media that can promote introduction of a nucleic acid into a host genome. While a plasmid is a form of vector that is most commonly used, all other forms of vectors that provide the same function and are known or about to be known in the art are suitable for use herein. See, for example, Pouwels et al., Cloning Vectors: A Laboratory Manual, 1985 and Supplements, Elsevier, N.Y. and Rodriguez et al. (Ed.), Vectors: A Survey of Molecular Cloning Vectors and Their Uses 1988, Buttersworth, Boston, Mass.

The term "expression system" refers to host cells and compatible vectors that can express a protein or a nucleic acid, which is carried and introduced into a host cell by the vector, under a suitable condition. Examples of common expression systems include *E. coli* host cells and plasmid vectors, insect host cells and baculovirus vectors, and mammalian host cells and vectors.

The expression of a nucleic acid encoding the polypeptide of SEQ ID NO: 2 and/or SEQ ID NO: 4 of the invention preferably can be executed by a conventional method in eukaryotic cells. Examples of suitable host cells for expressing a nucleic acid include high eukaryotes, as well as tissue culture cell lines established from animal cells (animal cells from both a non-mammalian origin (e.g., insect cells) and mammalian original (e.g., humans, primates, and rodents)).

Higher eukaryotic tissue culture cells can also be used for recombinant generation of the polypeptide set forth in SEQ ID NO: 2 and/or SEQ ID NO: 4 of the invention (or variant thereof). Any higher eukaryotic tissue culture cell line (including insect baculovirus expression system) can be used, but mammalian cells are preferable. Transformation, transfection, and proliferation of such cells are conventional procedures. Examples of useful cell lines include HeLa cells, Chinese hamster ovary (CHO) cell lines, J774 cells, Caco2 cells, baby rat kidney (BRK) cell lines, insect cell lines, avian cell lines, and monkey (COS) cell lines. Expression vectors for such cell lines generally include an origin of replication, promoter, translation initiation site, RNA splicing site (when genomic DNA is used), polyadenylation site, and transcription termination site. Such vectors also generally include a selector gene or an amplification gene. Examples of suitable expression vectors include plasmids, viruses, and retroviruses carrying a promotor derived from a source such as an adenovirus, SV40, parvovirus, vaccinia virus, or cytomegalovirus. Examples of expression vectors include pCR® 3.1, pCDNA1, pCD (Okayama et al., (1985) Mol. Cell Biol. 5: 1136), pMC1neo Poly-A (Thomas et al., (1987) Cell 51: 503), pREP8, pSVSPORT and derivatives thereof, and baculovirus vectors (e.g., pAC373 and pAC610).

As used herein, "operably linked" refers to expression (operation) of a desired sequence being placed under the control of a certain transcription/translation regulatory sequence (e.g., a promoter, an enhancer, or the like) or translation regulatory sequence. To operably link a promotor to a gene, the promotor is generally placed immediately upstream of the gene, but the promotor does not necessarily need to be placed adjacent to the gene.

The technology for introducing a nucleic acid molecule into a cell can be any technology herein. Examples thereof include transformation, transduction, transfection, and the like. Such nucleic acid molecule introducing technologies are well known and conventionally used in the art, and are described in, for example, Ausubel F. A. et al. (Ed.) (1988), Current Protocols in Molecular Biology, Wiley, New York, N.Y.; Sambrook J et al., (1987) Molecular Cloning: A Laboratory Manual, 2nd Ed. and 3rd Ed. thereof, Cold Spring Harbor Laboratory Press, Cold Spring Harbor, N.Y., Bessatsu Jikken Igaku [*Experimental Medicine, Supplemental Volume*], "Idenshi Donyu & Hatsugen Kaiseki Jikken Ho" [*Experimental Methods for Gene Transfer & Expression Analysis*], Yodosha, 1997, or the like. Gene transfer can be confirmed by using the methods described herein such as Northern blot or Western blot analysis or other well-known and conventional technologies.

Any method described above for introducing a DNA into a cell can be used as the method of introducing a vector. Examples thereof include transfection, transduction, transformation (e.g., calcium phosphate method, liposome method, DEAE dextran method, electroporation, method using a particle gun (gene gun), and the like), and the like.

(Membrane Protein Extracted from Pacific Krill)

The present invention can utilize a membrane protein extracted from Pacific krill (e.g., crude purified material comprising a membrane protein extracted from Pacific krill) as a source of lipoxygenase and/or a composition comprising lipoxygenase. Such a composition can be used for subjecting a substrate to a lipoxygenase enzymatic reaction. Various well known methods can be used as a method of extracting a membrane protein from Pacific krill. For example, a crude purified material comprising a membrane protein from Pacific krill can be prepared by pulverizing Pacific krill (can be, for example, cryopreserved Pacific krill or refrigerated Pacific krill) in a buffer, re-suspending a membrane protein fraction precipitated by centrifugation in a buffer, and centrifuging the suspension again.

Besides the preparation method using centrifugation described above, filtration, precipitation using a surfactant, precipitation using a solvent such as ethanol, and combination thereof can also be utilized for extracting a membrane protein from Pacific krill. This method can be used not only for the preparation of a membrane protein of Pacific krill, but also for the preparation of a membrane protein of membrane proteins of an organism belonging to Malacostraca, an organism belonging to Euphausiacea, or an organism belonging to Decapoda. Examples of organisms belonging to Malacostraca used herein include organisms belonging to Euphausiacea and organisms belonging to Decapoda. Examples of organisms belonging to Euphausiacea include, but are not limited to, organisms belonging to *Euphausia* and organisms belonging to *Meganyctiphanes* such as Pacific krill (*Euphausia pacifica*), Antarctic krill (*Euphausia superba*), and Northern krill (*Meganyctiphanes norvegica*). Examples of organisms belonging to Decapoda include, but are not limited to, organisms belonging to *Acetes*, organisms belonging to Marsupenaeus, organisms belonging to *Erimacrus*, and organisms belonging to Paralithodes, such as akiami paste shrimp (*Acetes japonicus*), kuruma shrimp (Marsupenaeus *japonicus*), hair crab (*Erimacrus isenbeckii*), and king crab (*Paralithodes camtschaticus*).

(Enzymatic Reaction Using Lipoxygenase of the Invention)

Examples of reactions of the lipoxygenase of the invention include, but are not limited to, physiological conditions. As a substrate of the lipoxygenase of the invention, an unsaturated fatty acid, especially a highly unsaturated fatty acid can be used. A highly unsaturated fatty acid can be a free fatty acid. Unsaturated fatty acid derivatives such as highly unsaturated fatty acid derivatives can also be used as a substrate. Examples of derivatives of highly unsaturated fatty acids include, but are not limited to, ethyl esters of a highly unsaturated fatty acid, triglycerides comprising a highly unsaturated fatty acid, diglycerides comprising a highly unsaturated fatty acid, monoglycerides comprising a highly unsaturated fatty acid, phospholipids comprising a highly unsaturated fatty acid, lysophospholipids comprising a highly unsaturated fatty acid, sphingolipids comprising a highly unsaturated fatty acid, glycolipids comprising a highly unsaturated fatty acid, and amidic derivatives of a highly unsaturated fatty acid (e.g., fatty acid amide such as ethanolamide of a highly unsaturated fatty acid). Derivatives of a highly unsaturated fatty acid also encompass esters of a highly unsaturated fatty acid. An unsaturated fatty acid ester (e.g., unsaturated fatty acid ethyl ester), especially a highly unsaturated fatty acid ester (e.g., highly unsaturated fatty acid ethyl ester), can also be used as a substrate for an enzymatic reaction. Examples of highly unsaturated fatty acids include, but are not limited to, docosahexaenoic acid (C22:6, DHA), eicosapentaenoic acid (C20:5, EPA), arachidonic acid (C20:4, AA), docosapentaenoic acid (C22:5, DPA), stearidonic acid (C18:4), linolenic acid (C18:3), linoleic acid (C18:2), tetracosahexaenoic acid (C24:6), eicosatetraenoic acid (C20:4, ETA), eicosatrienoic acid (C20:3), and the like.

When performing an enzymatic reaction, any of a purified protein, a crude purified material comprising a membrane protein (e.g., composition comprising a Pacific krill membrane protein), and recombinantly expressed protein can be used.

The lipoxygenase of the invention, since it is an 8-lipoxygenase, enables highly efficient generation of an 8-hydroxyeicosatetraenoic acid from an arachidonic acid, highly efficient generation of an 8-hydroxyeicosapentaenoic acid from an eicosapentaenoic acid, and highly efficient generation of a 10-hydroxydocosahexaenoic acid from a docosahexaenoic acid.

Examples of organisms belonging to Malacostraca used herein include organisms belonging to Euphausiacea and organisms belonging to Decapoda. Examples of organisms belonging to Euphausiacea include, but are not limited to, organisms belonging to *Euphausia* and organisms belonging to *Meganyctiphanes* such as Pacific krill (*Euphausia pacifica*), Antarctic krill (*Euphausia superba*), and Northern krill (*Meganyctiphanes norvegica*). Examples of organisms belonging to Decapoda include, but are not limited to, organisms belonging to *Acetes*, organisms belonging to Marsupenaeus, organisms belonging to *Erimacrus*, and organisms belonging to Paralithodes, such as akiami paste shrimp (*Acetes japonicus*), kuruma shrimp (Marsupenaeus *japonicus*), hair crab (*Erimacrus isenbeckii*), and king crab (*Paralithodes camtschaticus*).

The isolation, identification, and use of the lipoxygenase of the invention is specifically described hereinafter based on Examples and the like. It should be noted that the present invention is not limited thereto.

EXAMPLES

Example 1

Isolation and identification of a lipoxygenase gene from Pacific krill (scientific name: *Euphausia pacifica*)

Total RNA was purified using a Lipid tissue RNA extraction kit (Qiagen) from *Euphausia pacifica* (N=4). To analyze the sequence of *Euphausia pacifica* RNA with a next generation sequencer, a library was created using TruSeq RNA Library Prep Kit v2 (Illumina), with the *Euphausia pacifica* RNA as the template. The base sequence of the library was analyzed using Illumina's next generation sequencer (MiSeq) to obtain about 20 Gb of base sequence data. The base sequence fragment data for *Euphausia pacifica* was analyzed with a base sequence assembly program: Trinity (https://github.com/trinityrnaseq/trinityrnaseq/wiki), resulting in 42,432 contig sequences. The N50 size of the resulting contig sequences was 1,487 b.

To narrow down candidates for the *Euphausia pacifica* lipoxigenase gene (Pacific krill Lipoxigenase, abbreviated as PK LOX) from the contig sequences, contigs encoding an amino acid sequence similar to human and mouse arachidonate 5-lipoxygenase, arachidonate 15-lipoxygenase, or arachidonate 12-lipoxygenase were searched using Blast (https://blast.ncbi.nlm.nih.gov/Blast.cgi). As a result of the search, three PK LOX candidate genes were obtained and named PK LOX1, 2, and 3. The amino acid sequences encoded by PK LOX1, 2, and 3 were analyzed using GENETYX-MAC (https://www.genetyx.co.jp/products/genetyx_mac_19/news.htm 1), which revealed that PK LOX1 is a gene encoding a lipoxygenase-like protein consisting of 691 amino acid sequences. The base sequence of PK LOX1 is set forth in SEQ ID NO: 1 (FIG. 1), and the amino acid sequence thereof is set forth in SEQ ID NO: 2 (FIG. 2).

Since amino acid sequences encoded by the PK LOX2 and PK LOX3 candidate genes obtained from the result of analysis with a next generation sequencer were short fragments that are sequences of 100 amino acids or less, the full-length cDNA sequence was analyzed by RACE, and the PK LOX2 and PK LOX3 DNA sequences were analyzed by sequencing using Sanger's method. The PK LOX2 gene obtained as a result of re-analysis was identified as PK LOX2, which is a 2061 bp DNA sequence encoding a lipoxygenase-like protein consisting of 686 amino acid sequences. The base sequence of PK LOX2 is set forth in SEQ ID NO: 3 (FIG. 3), and the amino acid sequence thereof is set forth in SEQ ID NO: 4 (FIG. 4). Since a base sequence encoding a protein with a length of 100 amino acids or more could not be found for PK LOX3 from RACE and cloning analysis, PK LOX3 was determined as a pseudogene and excluded from experiments in Example 2 and thereafter.

Example 2

Expression of PK LOX1 and PK LOX2

Cloning was performed by using a DNA homologous recombination enzyme NEBilder (NEB) with a base sequence (ATGTCGTACTACCATCACCATCACCAT-CACGATTACGATATCCCAACGACCGAAAACC TGT-ATTTTCAGGGCGCCATG) encoding 6×His and TEV recognition site set forth in SEQ ID NO: 9 on the 5' side of a PK LOX1 base sequence amplified by PCR using a primer of SEQ ID NO: 5 ((PK LOX1 Forward Primer) (His+PK LOX1) 5'-TGTATTTTCAGGGCGCCATGGCGCCAAT-TAAGGAAAAGAA-3') and a primer of SEQ ID NO: 6 ((PK LOX1 Reverse Primer) 5'-agtgagctcgtcgacgtaggctaTA-CACTGATGGCATTTGGAA-3') and a PK LOX2 base sequence amplified using a primer of SEQ ID NO: 7 ((PK LOX2 Forward Primer) (His+PK LOX2) 5'-TGTAT-TTTCAGGGCGCCATGGTAGCGCTGCGCTGCTTCAA-3') and a primer of SEQ ID NO: 8 ((PK LOX2 Reverse Primer) 5'-agtgagctcgtcgacgtaggctaAATACTTATTGCAT-TTGGAA-3') on pFastBacl plasmid (Invitrogen) linearized with a restriction enzyme StuI (Takara). The pFASTBac1 plasmid cloning PK LOX1 and 2 was transformed into DH10Bac (Invitrogen) having bacmid and helper to obtain bacmid expressing PK LOX1 and 2. The bacmid purified using EasyPure or NucleoBond Xtra Midi (MACHEREY-NAGEL) was introduced, by using Cellfectin II Reagent, into Sf9 insect cells (Invitrogen) cultured using Grace's insect medium (Invitrogen). The Sf9 insect cells introduced with Bacmid were collected one week after the introduction. The medium at this point was used as the P1 virus stock. The collected Sf9 insect cells were dissolved on ice for 1 hour using a RIPA buffer. The supernatant after 10 minutes of centrifugation at 20,000 g was prepared as a protein solution. The resulting protein solution was separated by SDS page, and detection was performed using anti-6×His antibodies (Abcam) after transferred onto a PVDF membrane. Protein bands were found at a position of 75 to 85 kDa for PK LOX1 and at a position of 70 to 75 kDa for PK LOX2 (FIG. 5).

Example 3

Measurement of Activity of PK LOX1

A P1 baculovirus stock prepared by cryopreserving a culture supernatant of Sf9 insect cells transduced with bacmid expressing PK LOX1 was added to a medium of Sf9 insect cells and cultured for 1 week. 50 μM of arachidonic acid, eicosapentaenoic acid, or docosahexaenoic acid was added to the medium of baculovirus infected cells, and the cells were centrifuged and collected after 4 hours of culture. After removing the medium from the Sf9 cells and adding acetonitrile to the cells and sonicating the cells, the solution was centrifuged for 10 minutes at 20,000 g, and the supernatant was used as an extract. 5 μL of the extract was subjected to high performance liquid chromatography/mass spectrometry system (LC-QTOFMS: Agilent) to analyze 8-HETE, 8-HEPE, and 10-HDoHE. Production of 8-HEPE was observed in a cell extract prepared by adding EPA to Sf9 insect cells that have expressed PK LOX1 and culturing the cells (FIG. 6A). It can be understood that PK LOX1 catalyzed position 8 specific oxidation of EPA in view of there being only one peak of m/z=317.22 detected in the PK LOX1 expressing Sf9 cell extract, the column retention time completely matching that of a standard product of 8-HEPE (FIG. 6A), and ion patterns obtained by MS/MS analysis matching those of a standard product of 8-HEPE (FIG. 6B). The 8-HETE content after adding an arachidonic acid, 8-HEPE content after adding an eicosapentaenoic acid, and 10-HDoHE content after adding a docosahexaenoic acid are higher in a PK LOX1 expressing Sf9 insect cell extract compared to an extract of EGFP expressing Sf9 insect cells used as a control. It was confirmed that 8-HETE, 8-HEPE, and 10-HDoHE production is induced by PK LOX1 expression (FIG. 6C). The specific activity of lipoxygenase demonstrated in FIG. 6C was up to about 2.5 µg/mg (8-HEPE/PK LOX1 expressing Sf9 cell protein). The activity was markedly stronger than the specific activity of lipoxygenases known in the art.

Example 4

Measurement of Activity of PK LOX2

A baculovirus stock expressing PK LOX2 obtained by the same method as PK LOX1 in Example 3 was prepared. Sf9 cells were infected therewith. After washing the Sf9 cells after two days from infection with PBS and centrifuging the cells at 1500 g, the cells were frozen at −80° C. after removing the PBS. 50 µL of 200 mM Tris-HCl (pH of 7.4) supplemented with EPA at a concentration of 50 µM was added to PK LOX2 expressing Sf9 cell pellets thawed on ice, and the pellets were incubated for 4 hours at 27° C. After adding 150 µL of acetonitrile (containing 1% formic acid) to the incubated solution and vortexing the solution, the solution was centrifuged for 10 minutes at 4° C. at 20,000 g. The supernatant was collected and 5 µL thereof was subjected to LC-QTOFMS to analyze 8-HEPE. 8-HEPE production was observed in PK LOX2 expressing Sf9 cells (FIG. 7). The specific activity of lipoxygenase demonstrated in FIG. 7 was up to about 3.2 ng/mg (8-HEPE/PK LOX2 expressing Sf9 cell protein). The activity was markedly stronger than the specific activity of lipoxygenases known in the art.

Example 5

8-HEPE Production Utilizing a Pacific Krill Membrane Protein 2 g of Pacific krill cryopreserved at −50° C. was crushed with a mortar and pestle. 100 mg thereof was dispensed in a 2 mL tube, and 1 mL of NP-40 Lysis Buffer (150 mM NaCl, 1% NP-40, 50 mM Tris-HCl (pH 8.0)) was added. The sample was crushed using a Dounce homogenizer. Subsequently, the sample was incubated for 30 minutes on ice and then centrifuged for 10 minutes at 4° C. at 20,000 g. The precipitated membrane protein fraction was resuspended in 1 mL of 200 mM Tris-HCl. The suspension was dispensed at 200 µL (20 mg) each and centrifuged for 10 minutes at 4° C. at 20,000 g. The Pacific krill membrane protein obtained as a precipitate was stored at −80° C. 25 µL of 200 mM Tris-HCl containing 1 mM EPA was added to 20 mg of Pacific krill membrane protein and reacted for 3 hours on ice. After adding 75 µL of acetonitrile containing 1% formic acid to the post-reaction solution and vortexing the mixture, the mixture was centrifuged for 10 minutes at 4° C. at 20,000 g. 5 µL of the supernatant after centrifugation was subjected to LC-QTOFMS to analyze 8-HEPE. 42 ng of 8-HEPE production was observed by reacting 20 mg of Pacific krill membrane protein with 73 µg of EPA for 3 hours on ice. A Pacific krill membrane protein prepared in this manner can be used as a lipoxygenase-containing composition. The specific activity of this lipoxygenase was up to about 2.1 ng/mg (8-HEPE/Pacific krill membrane protein). The activity was markedly stronger than the specific activity of lipoxygenases known in the art.

The present invention has been exemplified above using preferred embodiments of the invention, but the present invention should not be interpreted to be limited to these embodiments. It is also understood that the scope of the present invention should be interpreted solely from the scope of Claims. It is understood that those skilled in the art can practice an equivalent scope from the specific descriptions of the preferred embodiments of the invention based on the description of the present invention and common general knowledge. It is understood that any patent, any patent application, and any references cited herein should be incorporated herein by reference in the same manner as the contents are specifically described herein.

INDUSTRIAL APPLICABILITY

The lipoxygenase provided by the present invention enables highly efficient generation of an 8-hydroxyeicosatetraenoic acid from an arachidonic acid, highly efficient generation of an 8-hydroxyeicosapentaenoic acid from an eicosapentaenoic acid, and highly efficient generation of a 10-hydroxydocosahexaenoic acid from a docosahexaenoic acid.

[Sequence Listing Free Text]

SEQ ID NO: 1 is a nucleic acid sequence of a lipoxygenase gene (PK LOX1) isolated from *Euphausia pacifica*.

SEQ ID NO: 2 is an amino acid sequence of a lipoxygenase (PK LOX1) isolated from *Euphausia pacifica*.

SEQ ID NO: 3 is a nucleic acid sequence of a lipoxygenase gene (PK LOX2) isolated from *Euphausia pacifica*.

SEQ ID NO: 4 is an amino acid sequence of a lipoxygenase (PK LOX2) isolated from *Euphausia pacifica*.

SEQ ID NO: 5 is a nucleic acid sequence of a forward primer for amplifying PK LOX1.

SEQ ID NO: 6 is a nucleic acid sequence of a reverse primer for amplifying PK LOX1.

SEQ ID NO: 7 is a nucleic acid sequence of a forward primer for amplifying PK LOX2.

SEQ ID NO: 8 is a nucleic acid sequence of a reverse primer for amplifying PK LOX2.

SEQ ID NO: 9 is a nucleic acid sequence encoding 6×His and TEV recognition site.

SEQ ID NO: 10 is an amino acid sequence encoded by SEQ ID NO: 9.

The invention claimed is:

1. A method of generating an oxide by reacting a polypeptide with a highly unsaturated fatty acid or a derivative of a highly unsaturated fatty acid, wherein the polypeptide is selected from the group consisting of:
   (a) a polypeptide comprising the amino acid sequence selected from the group consisting of SEQ ID NO: 2 and SEQ ID NO: 4; and
   (b) a polypeptide encoded by a nucleic acid comprising the nucleic acid sequence selected from the group consisting of SEQ ID NO: 1 and SEQ ID NO: 3;
   wherein the polypeptide has activity selected from the group consisting of:
   (1) activity to oxidize carbon at position 8 of an arachidonic acid;
   (2) activity to oxidize carbon at position 8 of an eicosapentaenoic acid; and
   (3) activity to oxidize carbon at position 10 of a docosahexaenoic acid.

2. The method of claim 1, wherein:
   the highly unsaturated fatty acid is an arachidonic acid, and the oxide is an 8-hydroxyeicosatetraenoic acid;
   the highly unsaturated fatty acid is an eicosapentaenoic acid, and the oxide is an 8-hydroxyeicosapentaenoic acid;
   the highly unsaturated fatty acid is a docosahexaenoic acid, and the oxide is a 10-hydroxydocosahexaenoic acid; and/or
   the highly unsaturated fatty acid is a docosapentaenoic acid, and the oxide is a 10-hydroxydocosapentaenoic acid.

3. The method of claim 2, wherein the highly unsaturated fatty acid is an eicosapentaenoic acid, and the oxide is an 8-hydroxyeicosapentaenoic acid.

4. A method of generating an oxide by reacting an 8-lipoxygenase derived from Malacostraca with a highly unsaturated fatty acid or a derivative of a highly unsaturated fatty acid, wherein the 8-lipoxygenase has activity selected from the group consisting of:
   (1) activity to oxidize carbon at position 8 of an arachidonic acid;
   (2) activity to oxidize carbon at position 8 of an eicosapentaenoic acid; and
   (3) activity to oxidize carbon at position 10 of a docosahexaenoic acid,
   wherein the 8-lipoxygenase comprises the amino acid sequence selected from the group consisting of SEQ ID NO: 2 and SEQ ID NO: 4.

5. The method of claim 4, wherein the 8-lipoxygenase is an 8-lipoxygenase derived from Euphausiacea or an 8-lipoxygenase derived from Decapoda.

6. The method of claim 4, wherein:
   the highly unsaturated fatty acid is an arachidonic acid, and the oxide is an 8-hydroxyeicosatetraenoic acid;
   the highly unsaturated fatty acid is an eicosapentaenoic acid, and the oxide is an 8-hydroxyeicosapentaenoic acid;
   the highly unsaturated fatty acid is a docosahexaenoic acid, and the oxide is a 10-hydroxydocosahexaenoic acid; and/or
   the highly unsaturated fatty acid is a docosapentaenoic acid, and the oxide is a 10-hydroxydocosapentaenoic acid.

7. The method of claim 6, wherein the highly unsaturated fatty acid is an eicosapentaenoic acid, and the oxide is an 8-hydroxyeicosapentaenoic acid.

* * * * *

SEQUENCE LISTING

```
<160> NUMBER OF SEQ ID NOS: 10

<210> SEQ ID NO 1
<211> LENGTH: 2076
<212> TYPE: DNA
<213> ORGANISM: Euphausia pacifica
```

```
<220> FEATURE:
<221> NAME/KEY: CDS
<222> LOCATION: (1)..(2076)

<400> SEQUENCE: 1 atg gcg cca att aag gaa aag aag tct ttt aag ctg act gct gca aca      48
Met Ala Pro Ile Lys Glu Lys Lys Ser Phe Lys Leu Thr Ala Ala Thr
1               5                   10                  15 ggg aat caa gat ggc gct ggt aca gat gcc aat gtg tat gtg acc ttt      96
Gly Asn Gln Asp Gly Ala Gly Thr Asp Ala Asn Val Tyr Val Thr Phe
            20                  25                  30 gag gat gaa gaa ggt cgt cgg acg aaa gag aaa aag ctt gat aag ctt     144
Glu Asp Glu Glu Gly Arg Arg Thr Lys Glu Lys Lys Leu Asp Lys Leu
        35                  40                  45 ctg tac aat gat ctg gag aag ggc aaa aag gac aag tat gac atc aat     192
Leu Tyr Asn Asp Leu Glu Lys Gly Lys Lys Asp Lys Tyr Asp Ile Asn
    50                  55                  60 gca cct gta gag ttt ggt gca gtg aag aag ttg cat gtc cac agg gat     240
Ala Pro Val Glu Phe Gly Ala Val Lys Lys Leu His Val His Arg Asp
65                  70                  75                  80 tca act gga ttg gga gac tcc tgg ttc tgt gac tac ttc gaa att aaa     288
Ser Thr Gly Leu Gly Asp Ser Trp Phe Cys Asp Tyr Phe Glu Ile Lys
                85                  90                  95 gat tta cgc ttc aaa ggc aac aat aat gag ccc agc cct acc aag aaa     336
Asp Leu Arg Phe Lys Gly Asn Asn Asn Glu Pro Ser Pro Thr Lys Lys
            100                 105                 110 gaa tac tac tat ttt ccc att cac cgt tgg atc agc tcc cag cac cgg     384
Glu Tyr Tyr Tyr Phe Pro Ile His Arg Trp Ile Ser Ser Gln His Arg
        115                 120                 125 tat gag ttt gac gag tat ggg aca tgt cta cca cag gca gac cca tgc     432
Tyr Glu Phe Asp Glu Tyr Gly Thr Cys Leu Pro Gln Ala Asp Pro Cys
    130                 135                 140 ata ggt cca cgt aaa gcg gat ttg gag gcc aaa aag agc tca tac aat     480
Ile Gly Pro Arg Lys Ala Asp Leu Glu Ala Lys Lys Ser Ser Tyr Asn
145                 150                 155                 160 tat gtg tac cgt att ggt gca atg gcg gct act gac acg gat gcc        528
Tyr Val Tyr Arg Ile Gly Ala Met Ala Ala Thr Asp Thr Thr Asp Ala
                165                 170                 175 tgc gtt ggt cat tgt gca cag gtg gag acc ctt cct gca gat gag aag     576
Cys Val Gly His Cys Ala Gln Val Glu Thr Leu Pro Ala Asp Glu Lys
            180                 185                 190 ttc tct gaa gat tat tat tgg aac ttt gca aca gat aag tta aaa ctc     624
Phe Ser Glu Asp Tyr Tyr Trp Asn Phe Ala Thr Asp Lys Leu Lys Leu
        195                 200                 205 ctg gca gaa acc aaa tgg atg gag tgg aca aac caa aca aaa tgg aat     672
Leu Ala Glu Thr Lys Trp Met Glu Trp Thr Asn Gln Thr Lys Trp Asn
    210                 215                 220 agt ctt tct gat ctc aga agt gtt tac aaa aag agt ctt gga gaa cct     720
Ser Leu Ser Asp Leu Arg Ser Val Tyr Lys Lys Ser Leu Gly Glu Pro
225                 230                 235                 240 aag tgc tta gat gtt tgg cgt gaa gac tgg tgg ttt gga cta caa cga     768
Lys Cys Leu Asp Val Trp Arg Glu Asp Trp Trp Phe Gly Leu Gln Arg
                245                 250                 255 cta caa ggg gtc aac cca gtt att att gag cta tgt act cag ata cct     816
Leu Gln Gly Val Asn Pro Val Ile Ile Glu Leu Cys Thr Gln Ile Pro
            260                 265                 270 gat aac cta gct gtg act gac acc act gtt gaa ggt ctc atg gat gac     864
Asp Asn Leu Ala Val Thr Asp Thr Thr Val Glu Gly Leu Met Asp Asp
        275                 280                 285 tta act ctc aat gaa gct tta gaa aat aag aaa ata ttt ata tgc gac     912
```

|     |     |     |     |     |     |     |     |     |     |     |     |     |     |     |     |     |
|---|---|---|---|---|---|---|---|---|---|---|---|---|---|---|---|---|
| Leu | Thr | Leu | Asn | Glu | Ala | Leu | Glu | Asn | Lys | Lys | Ile | Phe | Ile | Cys | Asp | |
| | 290 | | | | 295 | | | | | 300 | | | | | | |

```
cta aag atc atg gat ggg cta tgc tgt aaa gaa aat cga gag ctt gca      960
Leu Lys Ile Met Asp Gly Leu Cys Cys Lys Glu Asn Arg Glu Leu Ala
305             310                 315                 320 gct ccc ttg gcg ttg ttc tac cta aat aaa gaa aat aag ctg ttg ccc     1008
Ala Pro Leu Ala Leu Phe Tyr Leu Asn Lys Glu Asn Lys Leu Leu Pro
                325                 330                 335 atc gca cta cag cta aaa cag gaa aaa gga gat gat aac cca gtt ttc     1056
Ile Ala Leu Gln Leu Lys Gln Glu Lys Gly Asp Asp Asn Pro Val Phe
            340                 345                 350 aca cct aag gat tct aag aat act tgg tta gtt gcg aag atg ttt tat     1104
Thr Pro Lys Asp Ser Lys Asn Thr Trp Leu Val Ala Lys Met Phe Tyr
        355                 360                 365 aac aat tct gaa gct cag cac cac caa gca ctg aca cat ctg ggt tac     1152
Asn Asn Ser Glu Ala Gln His His Gln Ala Leu Thr His Leu Gly Tyr
    370                 375                 380 aca cat ctc ctc atg gag gga gta gtg gtc tgc aca cac aga aac ctc     1200
Thr His Leu Leu Met Glu Gly Val Val Val Cys Thr His Arg Asn Leu
385                 390                 395                 400 tca cct tca cat cca ctc ttc aag ctt atg gca ccg cat ttc ttg ttt     1248
Ser Pro Ser His Pro Leu Phe Lys Leu Met Ala Pro His Phe Leu Phe
                405                 410                 415 ctc ttg gcc att aac tcg cgt ggt ctt gaa aag tta gtt tcc gaa ggt     1296
Leu Leu Ala Ile Asn Ser Arg Gly Leu Glu Lys Leu Val Ser Glu Gly
            420                 425                 430 gga tgg gtt gat tgc tgc atg aca cag ggc ctt tgt ggc atc ttg gat     1344
Gly Trp Val Asp Cys Cys Met Thr Gln Gly Leu Cys Gly Ile Leu Asp
        435                 440                 445 cta atg aag cga gga ttt gaa gca tgg aca tac aca aag ttt ggc tcg     1392
Leu Met Lys Arg Gly Phe Glu Ala Trp Thr Tyr Thr Lys Phe Gly Ser
    450                 455                 460 gtt tct gca gag ctt gaa gcc cgt ggt gta tta aac aaa gat gtt ctt     1440
Val Ser Ala Glu Leu Glu Ala Arg Gly Val Leu Asn Lys Asp Val Leu
465                 470                 475                 480 cca tat tat cca tat aga gac gat gct cta cct cta ttt gct gaa atc     1488
Pro Tyr Tyr Pro Tyr Arg Asp Asp Ala Leu Pro Leu Phe Ala Glu Ile
                485                 490                 495 aga aaa tat gtc aaa act att gtt gag cac cac tat gat aat gaa gat     1536
Arg Lys Tyr Val Lys Thr Ile Val Glu His His Tyr Asp Asn Glu Asp
            500                 505                 510 aag atg aaa gaa gac tgg gag tta aaa agc tgg agg gag gag tta gcc     1584
Lys Met Lys Glu Asp Trp Glu Leu Lys Ser Trp Arg Glu Glu Leu Ala
        515                 520                 525 aag cag cgg agt gaa aat gga gtt gga ctt gct gat atc ccg ggc tcg     1632
Lys Gln Arg Ser Glu Asn Gly Val Gly Leu Ala Asp Ile Pro Gly Ser
    530                 535                 540 aaa gaa gat ggt ttc aat agt gtg gat gaa gta gta gat gtg gtg aca     1680
Lys Glu Asp Gly Phe Asn Ser Val Asp Glu Val Val Asp Val Val Thr
545                 550                 555                 560 atg att att tca aca tgc tct ctt ggt cat gct gca tca aac ttc cag     1728
Met Ile Ile Ser Thr Cys Ser Leu Gly His Ala Ala Ser Asn Phe Gln
                565                 570                 575 cag tat gaa cag tac gga tat gtg cca aat tac cct ggt att ctc atg     1776
Gln Tyr Glu Gln Tyr Gly Tyr Val Pro Asn Tyr Pro Gly Ile Leu Met
            580                 585                 590 tct acc ttg cct aaa gaa aag aaa gag tat aca gaa gaa gaa atc atg     1824
Ser Thr Leu Pro Lys Glu Lys Lys Glu Tyr Thr Glu Glu Glu Ile Met
        595                 600                 605
```

-continued

| | | | | | | | | | | | | | | | |
|---|---|---|---|---|---|---|---|---|---|---|---|---|---|---|---|
| cag | atc | ctc | cca | gac | aag | cgg | atg | act | ttg | gat | atc | atg | gtc | atc | aca |
| Gln | Ile | Leu | Pro | Asp | Lys | Arg | Met | Thr | Leu | Asp | Ile | Met | Val | Ile | Thr |
| | 610 | | | | 615 | | | | 620 | | | | | | |

1872

| | | | | | | | | | | | | | | | |
|---|---|---|---|---|---|---|---|---|---|---|---|---|---|---|---|
| aag | cta | ctg | tca | acc | aaa | gga | aca | caa | agt | ctc | ggg | gac | ttt | gaa | atg |
| Lys | Leu | Leu | Ser | Thr | Lys | Gly | Thr | Gln | Ser | Leu | Gly | Asp | Phe | Glu | Met |
| 625 | | | | | 630 | | | | | 635 | | | | | 640 |

1920

| | | | | | | | | | | | | | | | |
|---|---|---|---|---|---|---|---|---|---|---|---|---|---|---|---|
| cag | tat | ctg | tat | gac | cct | gta | gga | gtc | cag | gcg | gct | aaa | gat | ttc | cgc |
| Gln | Tyr | Leu | Tyr | Asp | Pro | Val | Gly | Val | Gln | Ala | Ala | Lys | Asp | Phe | Arg |
| | | | | 645 | | | | | 650 | | | | | 655 | |

1968

| | | | | | | | | | | | | | | | |
|---|---|---|---|---|---|---|---|---|---|---|---|---|---|---|---|
| aaa | aac | ctt | gat | cga | ttg | agt | aaa | aaa | aat | aaa | ctt | gaa | aat | gtt | gat |
| Lys | Asn | Leu | Asp | Arg | Leu | Ser | Lys | Lys | Asn | Lys | Leu | Glu | Asn | Val | Asp |
| | | | | 660 | | | | 665 | | | | 670 | | | |

2016

| | | | | | | | | | | | | | | | |
|---|---|---|---|---|---|---|---|---|---|---|---|---|---|---|---|
| cga | caa | tgg | gac | ttt | gat | tgg | ctt | gat | cca | gaa | ttt | gtt | cca | aat | gcc |
| Arg | Gln | Trp | Asp | Phe | Asp | Trp | Leu | Asp | Pro | Glu | Phe | Val | Pro | Asn | Ala |
| | | | 675 | | | | 680 | | | | 685 | | | | |

2064

| | | |
|---|---|---|
| atc | agt | gta taa |
| Ile | Ser | Val |
| | | 690 |

2076

<210> SEQ ID NO 2
<211> LENGTH: 691
<212> TYPE: PRT
<213> ORGANISM: Euphausia pacifica

<400> SEQUENCE: 2

Met Ala Pro Ile Lys Glu Lys Lys Ser Phe Lys Leu Thr Ala Ala Thr
1               5                   10                  15

Gly Asn Gln Asp Gly Ala Gly Thr Asp Ala Asn Val Tyr Val Thr Phe
                20                  25                  30

Glu Asp Glu Glu Gly Arg Arg Thr Lys Glu Lys Lys Leu Asp Lys Leu
            35                  40                  45

Leu Tyr Asn Asp Leu Glu Lys Gly Lys Lys Asp Lys Tyr Asp Ile Asn
    50                  55                  60

Ala Pro Val Glu Phe Gly Ala Val Lys Lys Leu His Val His Arg Asp
65                  70                  75                  80

Ser Thr Gly Leu Gly Asp Ser Trp Phe Cys Asp Tyr Phe Glu Ile Lys
                85                  90                  95

Asp Leu Arg Phe Lys Gly Asn Asn Asn Glu Pro Ser Pro Thr Lys Lys
            100                 105                 110

Glu Tyr Tyr Tyr Phe Pro Ile His Arg Trp Ile Ser Ser Gln His Arg
        115                 120                 125

Tyr Glu Phe Asp Glu Tyr Gly Thr Cys Leu Pro Gln Ala Asp Pro Cys
    130                 135                 140

Ile Gly Pro Arg Lys Ala Asp Leu Glu Ala Lys Lys Ser Ser Tyr Asn
145                 150                 155                 160

Tyr Val Tyr Arg Ile Gly Ala Met Ala Ala Thr Asp Thr Thr Asp Ala
                165                 170                 175

Cys Val Gly His Cys Ala Gln Val Glu Thr Leu Pro Ala Asp Glu Lys
            180                 185                 190

Phe Ser Glu Asp Tyr Tyr Trp Asn Phe Ala Thr Asp Lys Leu Lys Leu
        195                 200                 205

Leu Ala Glu Thr Lys Trp Met Glu Trp Thr Asn Gln Thr Lys Trp Asn
    210                 215                 220

Ser Leu Ser Asp Leu Arg Ser Val Tyr Lys Lys Ser Leu Gly Glu Pro
225                 230                 235                 240

Lys Cys Leu Asp Val Trp Arg Glu Asp Trp Trp Phe Gly Leu Gln Arg
                245                 250                 255

```
Leu Gln Gly Val Asn Pro Val Ile Ile Glu Leu Cys Thr Gln Ile Pro
            260                 265                 270

Asp Asn Leu Ala Val Thr Asp Thr Val Glu Gly Leu Met Asp Asp
            275                 280                 285

Leu Thr Leu Asn Glu Ala Leu Glu Asn Lys Lys Ile Phe Ile Cys Asp
            290                 295                 300

Leu Lys Ile Met Asp Gly Leu Cys Cys Lys Glu Asn Arg Glu Leu Ala
305                 310                 315                 320

Ala Pro Leu Ala Leu Phe Tyr Leu Asn Lys Glu Asn Lys Leu Leu Pro
                325                 330                 335

Ile Ala Leu Gln Leu Lys Gln Glu Lys Gly Asp Asn Pro Val Phe
            340                 345                 350

Thr Pro Lys Asp Ser Lys Asn Thr Trp Leu Val Ala Lys Met Phe Tyr
            355                 360                 365

Asn Asn Ser Glu Ala Gln His His Gln Ala Leu Thr His Leu Gly Tyr
            370                 375                 380

Thr His Leu Leu Met Glu Gly Val Val Cys Thr His Arg Asn Leu
385                 390                 395                 400

Ser Pro Ser His Pro Leu Phe Lys Leu Met Ala Pro His Phe Leu Phe
                405                 410                 415

Leu Leu Ala Ile Asn Ser Arg Gly Leu Glu Lys Leu Val Ser Glu Gly
            420                 425                 430

Gly Trp Val Asp Cys Cys Met Thr Gln Gly Leu Cys Gly Ile Leu Asp
            435                 440                 445

Leu Met Lys Arg Gly Phe Glu Ala Trp Thr Tyr Thr Lys Phe Gly Ser
            450                 455                 460

Val Ser Ala Glu Leu Glu Ala Arg Gly Val Leu Asn Lys Asp Val Leu
465                 470                 475                 480

Pro Tyr Tyr Pro Tyr Arg Asp Asp Ala Leu Pro Leu Phe Ala Glu Ile
                485                 490                 495

Arg Lys Tyr Val Lys Thr Ile Val Glu His His Tyr Asp Asn Glu Asp
            500                 505                 510

Lys Met Lys Glu Asp Trp Glu Leu Lys Ser Trp Arg Glu Glu Leu Ala
            515                 520                 525

Lys Gln Arg Ser Glu Asn Gly Val Gly Leu Ala Asp Ile Pro Gly Ser
530                 535                 540

Lys Glu Asp Gly Phe Asn Ser Val Asp Glu Val Asp Val Val Thr
545                 550                 555                 560

Met Ile Ile Ser Thr Cys Ser Leu Gly His Ala Ala Ser Asn Phe Gln
                565                 570                 575

Gln Tyr Glu Gln Tyr Gly Tyr Val Pro Asn Tyr Pro Gly Ile Leu Met
            580                 585                 590

Ser Thr Leu Pro Lys Glu Lys Glu Tyr Thr Glu Glu Ile Met
            595                 600                 605

Gln Ile Leu Pro Asp Lys Arg Met Thr Leu Asp Ile Met Val Ile Thr
            610                 615                 620

Lys Leu Leu Ser Thr Lys Gly Thr Gln Ser Leu Gly Asp Phe Glu Met
625                 630                 635                 640

Gln Tyr Leu Tyr Asp Pro Val Gly Val Gln Ala Ala Lys Asp Phe Arg
                645                 650                 655

Lys Asn Leu Asp Arg Leu Ser Lys Lys Asn Lys Leu Glu Asn Val Asp
            660                 665                 670
```

```
Arg Gln Trp Asp Phe Asp Trp Leu Asp Pro Glu Phe Val Pro Asn Ala
            675                 680                 685
Ile Ser Val
    690

<210> SEQ ID NO 3
<211> LENGTH: 2061
<212> TYPE: DNA
<213> ORGANISM: Euphausia pacifica
<220> FEATURE:
<221> NAME/KEY: CDS
<222> LOCATION: (1)..(2061)

<400> SEQUENCE: 3 atg gta gcg ctg cgc tgc ttc aaa cca gag gaa atg cat att ttt aca      48
Met Val Ala Leu Arg Cys Phe Lys Pro Glu Glu Met His Ile Phe Thr
1               5                  10                  15 ata tgt gga ctt ttt ttg gcg gca atg gag gtc tca aat gct tat cta      96
Ile Cys Gly Leu Phe Leu Ala Ala Met Glu Val Ser Asn Ala Tyr Leu
            20                  25                  30 tgt aat aac aac ttt ttg gtg act gtg aag act ggt tat ggg aca gat     144
Cys Asn Asn Asn Phe Leu Val Thr Val Lys Thr Gly Tyr Gly Thr Asp
        35                  40                  45 gct ggc tca aat gca agt gtg ata tta gta tta gaa gat caa aat aga     192
Ala Gly Ser Asn Ala Ser Val Ile Leu Val Leu Glu Asp Gln Asn Arg
    50                  55                  60 aat gaa att aga aat tgg tta agt att ccg aaa caa gat gaa act gga     240
Asn Glu Ile Arg Asn Trp Leu Ser Ile Pro Lys Gln Asp Glu Thr Gly
65                  70                  75                  80 aat cat agg ata cct ata cca acg agt ttt gga aga ata gtg act gta     288
Asn His Arg Ile Pro Ile Pro Thr Ser Phe Gly Arg Ile Val Thr Val
                85                  90                  95 gaa tta gcc cta gat tat aag ctt gct ccc gat tgg tat tgt gag gat     336
Glu Leu Ala Leu Asp Tyr Lys Leu Ala Pro Asp Trp Tyr Cys Glu Asp
            100                 105                 110 atc ttt att gaa gat cct cga cta aat gac aga tta tat ttt cca att     384
Ile Phe Ile Glu Asp Pro Arg Leu Asn Asp Arg Leu Tyr Phe Pro Ile
        115                 120                 125 gat cga aga att caa ggt aac cag ttt tat gat ttt caa aac tat gcc     432
Asp Arg Arg Ile Gln Gly Asn Gln Phe Tyr Asp Phe Gln Asn Tyr Ala
    130                 135                 140 act tgc cta cca caa ttt gac caa aat agt ata agc aga aga ttg act     480
Thr Cys Leu Pro Gln Phe Asp Gln Asn Ser Ile Ser Arg Arg Leu Thr
145                 150                 155                 160 cta caa aag aag aga gaa gat tat caa cta tct tac gac cgt aca gct     528
Leu Gln Lys Lys Arg Glu Asp Tyr Gln Leu Ser Tyr Asp Arg Thr Ala
                165                 170                 175 gca atg gtt aaa gat ctc cca cag gat gaa ata ttt cat cag gat tat     576
Ala Met Val Lys Asp Leu Pro Gln Asp Glu Ile Phe His Gln Asp Tyr
            180                 185                 190 att tct agc att aga gca ata caa aag acg tct att gat gac cag ata     624
Ile Ser Ser Ile Arg Ala Ile Gln Lys Thr Ser Ile Asp Asp Gln Ile
        195                 200                 205 cct ctg ctc caa gca tgg cag agt tct aac aat atc agc gca ttt ttt     672
Pro Leu Leu Gln Ala Trp Gln Ser Ser Asn Asn Ile Ser Ala Phe Phe
    210                 215                 220 gga gga gac ttt tac atg cca cag agt ata cag ttt tgg aaa gaa gat     720
Gly Gly Asp Phe Tyr Met Pro Gln Ser Ile Gln Phe Trp Lys Glu Asp
225                 230                 235                 240 gca tgg ttt ggt gct cag cgt gtt caa ggg ata gta cca aat att att     768
Ala Trp Phe Gly Ala Gln Arg Val Gln Gly Ile Val Pro Asn Ile Ile
```

-continued

|     |     |     |     |     | 245 |     |     |     |     | 250 |     |     |     |     | 255 |     |      |
| --- | --- | --- | --- | --- | --- | --- | --- | --- | --- | --- | --- | --- | --- | --- | --- | --- | ---- |
| gaa | ctt | tgt | aaa | caa | att | cca | gat | aaa | tta | gga | gtg | aca | gaa | gat | acc |     | 816  |
| Glu | Leu | Cys | Lys | Gln | Ile | Pro | Asp | Lys | Leu | Gly | Val | Thr | Glu | Asp | Thr |     |      |
|     |     |     | 260 |     |     |     |     | 265 |     |     |     |     | 270 |     |     |     |      |

| att | agt | ggg | ctt | cta | gaa | ggc | tct | act | ctc | caa | cag | gca | tta | aag | aac | 864 |
| Ile | Ser | Gly | Leu | Leu | Glu | Gly | Ser | Thr | Leu | Gln | Gln | Ala | Leu | Lys | Asn |     |
|     |     | 275 |     |     |     |     | 280 |     |     |     |     | 285 |     |     |     |     |

| aac | aaa | ata | ttt | ata | tcc | gac | ctg | gaa | ctc | tta | gat | ggg | ata | cag | tat | 912 |
| Asn | Lys | Ile | Phe | Ile | Ser | Asp | Leu | Glu | Leu | Leu | Asp | Gly | Ile | Gln | Tyr |     |
|     | 290 |     |     |     |     | 295 |     |     |     |     | 300 |     |     |     |     |     |

| agt | gga | gtg | tgg | agt | gac | aat | gca | gat | cat | gcc | gcg | cct | att | tcg | gtt | 960 |
| Ser | Gly | Val | Trp | Ser | Asp | Asn | Ala | Asp | His | Ala | Ala | Pro | Ile | Ser | Val |     |
| 305 |     |     |     | 310 |     |     |     |     | 315 |     |     |     |     | 320 |     |     |

| ttt | tat | ctc | aat | aaa | ata | gat | caa | tta | atg | ccc | atc | gca | att | cag | ctc | 1008 |
| Phe | Tyr | Leu | Asn | Lys | Ile | Asp | Gln | Leu | Met | Pro | Ile | Ala | Ile | Gln | Leu |      |
|     |     |     |     | 325 |     |     |     |     | 330 |     |     |     |     | 335 |     |      |

| aga | caa | cag | aaa | ggt | cca | aaa | aac | cct | gtc | tat | acc | cct | aaa | gac | cca | 1056 |
| Arg | Gln | Gln | Lys | Gly | Pro | Lys | Asn | Pro | Val | Tyr | Thr | Pro | Lys | Asp | Pro |      |
|     |     |     | 340 |     |     |     |     | 345 |     |     |     |     | 350 |     |     |      |

| cca | aat | acc | tgg | ctt | gtt | gct | aag | ata | tat | tat | aac | aat | gca | gaa | tcc | 1104 |
| Pro | Asn | Thr | Trp | Leu | Val | Ala | Lys | Ile | Tyr | Tyr | Asn | Asn | Ala | Glu | Ser |      |
|     |     | 355 |     |     |     |     | 360 |     |     |     |     | 365 |     |     |     |      |

| cag | ttc | cat | caa | att | ctg | gtt | cat | ttt | ggc | tat | acc | cat | atg | ata | atg | 1152 |
| Gln | Phe | His | Gln | Ile | Leu | Val | His | Phe | Gly | Tyr | Thr | His | Met | Ile | Met |      |
|     | 370 |     |     |     |     | 375 |     |     |     |     | 380 |     |     |     |     |      |

| gat | ggc | atc | gct | aca | agt | atg | aac | cgg | caa | ctg | tca | cca | tca | cat | ccc | 1200 |
| Asp | Gly | Ile | Ala | Thr | Ser | Met | Asn | Arg | Gln | Leu | Ser | Pro | Ser | His | Pro |      |
| 385 |     |     |     | 390 |     |     |     |     | 395 |     |     |     |     | 400 |     |      |

| gtg | ttc | aaa | atc | ctg | aag | ccg | cac | ttt | cta | tat | ctt | ctg | gct | att | aac | 1248 |
| Val | Phe | Lys | Ile | Leu | Lys | Pro | His | Phe | Leu | Tyr | Leu | Leu | Ala | Ile | Asn |      |
|     |     |     |     | 405 |     |     |     |     | 410 |     |     |     |     | 415 |     |      |

| aga | tta | gga | gaa | caa | gaa | tta | ttt | gtg | ccc | caa | gga | gtg | ttc | cca | tat | 1296 |
| Arg | Leu | Gly | Glu | Gln | Glu | Leu | Phe | Val | Pro | Gln | Gly | Val | Phe | Pro | Tyr |      |
|     |     |     | 420 |     |     |     |     | 425 |     |     |     |     | 430 |     |     |      |

| ttt | tct | att | ggc | tta | gat | ggc | atg | aac | caa | cta | ctg | gca | aag | gca | gtt | 1344 |
| Phe | Ser | Ile | Gly | Leu | Asp | Gly | Met | Asn | Gln | Leu | Leu | Ala | Lys | Ala | Val |      |
|     |     | 435 |     |     |     |     | 440 |     |     |     |     | 445 |     |     |     |      |

| cca | caa | ttc | acc | ctc | gca | aga | gct | att | gga | tca | gtt | gaa | tct | gac | gcc | 1392 |
| Pro | Gln | Phe | Thr | Leu | Ala | Arg | Ala | Ile | Gly | Ser | Val | Glu | Ser | Asp | Ala |      |
| 450 |     |     |     | 455 |     |     |     |     | 460 |     |     |     |     |     |     |      |

| agg | gct | cgt | gga | gtt | tgg | gat | aaa | cag | gtt | ctc | ccg | tat | tac | cca | ttt | 1440 |
| Arg | Ala | Arg | Gly | Val | Trp | Asp | Lys | Gln | Val | Leu | Pro | Tyr | Tyr | Pro | Phe |      |
| 465 |     |     |     | 470 |     |     |     |     | 475 |     |     |     |     | 480 |     |      |

| aga | gat | gat | gcg | cac | tct | atg | tac | aac | atc | atc | aag | aaa | tat | gcc | act | 1488 |
| Arg | Asp | Asp | Ala | His | Ser | Met | Tyr | Asn | Ile | Ile | Lys | Lys | Tyr | Ala | Thr |      |
|     |     |     |     | 485 |     |     |     |     | 490 |     |     |     |     | 495 |     |      |

| aaa | gtt | att | tat | tat | tat | tat | aat | aca | cca | gga | aaa | att | atc | aat | gat | 1536 |
| Lys | Val | Ile | Tyr | Tyr | Tyr | Tyr | Asn | Thr | Pro | Gly | Lys | Ile | Ile | Asn | Asp |      |
|     |     |     | 500 |     |     |     |     | 505 |     |     |     |     | 510 |     |     |      |

| atg | gag | ctg | cag | agg | tgg | cgt | act | gag | ctt | gct | aag | ccc | aga | gct | caa | 1584 |
| Met | Glu | Leu | Gln | Arg | Trp | Arg | Thr | Glu | Leu | Ala | Lys | Pro | Arg | Ala | Gln |      |
|     |     |     | 515 |     |     |     |     | 520 |     |     |     |     | 525 |     |     |      |

| gga | ggt | gtt | ggt | atc | cct | gat | ctt | cct | gga | tct | gat | aca | gca | ggt | ttc | 1632 |
| Gly | Gly | Val | Gly | Ile | Pro | Asp | Leu | Pro | Gly | Ser | Asp | Thr | Ala | Gly | Phe |      |
|     | 530 |     |     |     |     | 535 |     |     |     |     | 540 |     |     |     |     |      |

| cgt | gac | att | aat | gaa | att | atc | gat | ttg | gta | aca | acc | att | atc | act | cat | 1680 |
| Arg | Asp | Ile | Asn | Glu | Ile | Ile | Asp | Leu | Val | Thr | Thr | Ile | Ile | Thr | His |      |
| 545 |     |     |     | 550 |     |     |     |     | 555 |     |     |     |     | 560 |     |      |

| agt | tca | gtt | ggt | cat | gca | gct | gtc | aac | ttc | ccc | atg | tat | gat | aca | tat | 1728 |

-continued

```
                Ser Ser Val Gly His Ala Ala Val Asn Phe Pro Met Tyr Asp Thr Tyr
                            565                 570                 575 gga tat ttc cca aat tac cct cca gat tta aat gaa gga cct cct ctg       1776
Gly Tyr Phe Pro Asn Tyr Pro Pro Asp Leu Asn Glu Gly Pro Pro Leu
            580                 585                 590 caa aaa atg tta tat aca gaa gat gag att atg agc tta ttc cct aat       1824
Gln Lys Met Leu Tyr Thr Glu Asp Glu Ile Met Ser Leu Phe Pro Asn
            595                 600                 605 ggg agc cat gcg ttc agg gtc agg gcc aca ata agg gtc tta tcg tgg       1872
Gly Ser His Ala Phe Arg Val Arg Ala Thr Ile Arg Val Leu Ser Trp
    610                 615                 620 caa gga acc aat gac tgt ggg gac ttt gaa aaa ata tac ctg tat gac       1920
Gln Gly Thr Asn Asp Cys Gly Asp Phe Glu Lys Ile Tyr Leu Tyr Asp
625                 630                 635                 640 cca gtc agt cag gaa gct caa gtt gaa ctc aga aaa gat ctt gct atg       1968
Pro Val Ser Gln Glu Ala Gln Val Glu Leu Arg Lys Asp Leu Ala Met
                645                 650                 655 ttt agc aag gaa gtg atg aac aga aat agt aaa aga ttt att ccg tat       2016
Phe Ser Lys Glu Val Met Asn Arg Asn Ser Lys Arg Phe Ile Pro Tyr
            660                 665                 670 aaa tat cta gac cca aat tat gtt cca aat gca ata agt att tag           2061
Lys Tyr Leu Asp Pro Asn Tyr Val Pro Asn Ala Ile Ser Ile
            675                 680                 685

<210> SEQ ID NO 4
<211> LENGTH: 686
<212> TYPE: PRT
<213> ORGANISM: Euphausia pacifica

<400> SEQUENCE: 4

Met Val Ala Leu Arg Cys Phe Lys Pro Glu Glu Met His Ile Phe Thr
1               5                   10                  15

Ile Cys Gly Leu Phe Leu Ala Ala Met Glu Val Ser Asn Ala Tyr Leu
            20                  25                  30

Cys Asn Asn Phe Leu Val Thr Val Lys Thr Gly Tyr Gly Thr Asp
        35                  40                  45

Ala Gly Ser Asn Ala Ser Val Ile Leu Val Leu Glu Asp Gln Asn Arg
    50                  55                  60

Asn Glu Ile Arg Asn Trp Leu Ser Ile Pro Lys Gln Asp Glu Thr Gly
65                  70                  75                  80

Asn His Arg Ile Pro Ile Pro Thr Ser Phe Gly Arg Ile Val Thr Val
                85                  90                  95

Glu Leu Ala Leu Asp Tyr Lys Leu Ala Pro Asp Trp Tyr Cys Glu Asp
            100                 105                 110

Ile Phe Ile Glu Asp Pro Arg Leu Asn Asp Arg Leu Tyr Phe Pro Ile
        115                 120                 125

Asp Arg Arg Ile Gln Gly Asn Gln Phe Tyr Asp Phe Gln Asn Tyr Ala
    130                 135                 140

Thr Cys Leu Pro Gln Phe Asp Gln Asn Ser Ile Ser Arg Arg Leu Thr
145                 150                 155                 160

Leu Gln Lys Lys Arg Glu Asp Tyr Gln Leu Ser Tyr Asp Arg Thr Ala
                165                 170                 175

Ala Met Val Lys Asp Leu Pro Gln Asp Glu Ile Phe His Gln Asp Tyr
            180                 185                 190

Ile Ser Ser Ile Arg Ala Ile Gln Lys Thr Ser Ile Asp Asp Gln Ile
        195                 200                 205

Pro Leu Leu Gln Ala Trp Gln Ser Ser Asn Asn Ile Ser Ala Phe Phe
```

-continued

```
            210                 215                 220
Gly Gly Asp Phe Tyr Met Pro Gln Ser Ile Gln Phe Trp Lys Glu Asp
225                 230                 235                 240

Ala Trp Phe Gly Ala Gln Arg Val Gln Gly Ile Val Pro Asn Ile Ile
                    245                 250                 255

Glu Leu Cys Lys Gln Ile Pro Asp Lys Leu Gly Val Thr Glu Asp Thr
                260                 265                 270

Ile Ser Gly Leu Leu Glu Gly Ser Thr Leu Gln Gln Ala Leu Lys Asn
                275                 280                 285

Asn Lys Ile Phe Ile Ser Asp Leu Glu Leu Leu Asp Gly Ile Gln Tyr
            290                 295                 300

Ser Gly Val Trp Ser Asp Asn Ala Asp His Ala Ala Pro Ile Ser Val
305                 310                 315                 320

Phe Tyr Leu Asn Lys Ile Asp Gln Leu Met Pro Ile Ala Ile Gln Leu
                    325                 330                 335

Arg Gln Gln Lys Gly Pro Lys Asn Pro Val Tyr Thr Pro Lys Asp Pro
                340                 345                 350

Pro Asn Thr Trp Leu Val Ala Lys Ile Tyr Tyr Asn Asn Ala Glu Ser
                355                 360                 365

Gln Phe His Gln Ile Leu Val His Phe Gly Tyr Thr His Met Ile Met
            370                 375                 380

Asp Gly Ile Ala Thr Ser Met Asn Arg Gln Leu Ser Pro Ser His Pro
385                 390                 395                 400

Val Phe Lys Ile Leu Lys Pro His Phe Leu Tyr Leu Leu Ala Ile Asn
                    405                 410                 415

Arg Leu Gly Glu Gln Glu Leu Phe Val Pro Gln Gly Val Phe Pro Tyr
                420                 425                 430

Phe Ser Ile Gly Leu Asp Gly Met Asn Gln Leu Leu Ala Lys Ala Val
                435                 440                 445

Pro Gln Phe Thr Leu Ala Arg Ala Ile Gly Ser Val Glu Ser Asp Ala
            450                 455                 460

Arg Ala Arg Gly Val Trp Asp Lys Gln Val Leu Pro Tyr Tyr Pro Phe
465                 470                 475                 480

Arg Asp Asp Ala His Ser Met Tyr Asn Ile Ile Lys Lys Tyr Ala Thr
                    485                 490                 495

Lys Val Ile Tyr Tyr Tyr Asn Thr Pro Gly Lys Ile Ile Asn Asp
                500                 505                 510

Met Glu Leu Gln Arg Trp Arg Thr Glu Leu Ala Lys Pro Arg Ala Gln
                515                 520                 525

Gly Gly Val Gly Ile Pro Asp Leu Pro Gly Ser Asp Thr Ala Gly Phe
            530                 535                 540

Arg Asp Ile Asn Glu Ile Asp Leu Val Thr Thr Ile Ile Thr His
545                 550                 555                 560

Ser Ser Val Gly His Ala Ala Val Asn Phe Pro Met Tyr Asp Thr Tyr
                    565                 570                 575

Gly Tyr Phe Pro Asn Tyr Pro Pro Asp Leu Asn Glu Gly Pro Pro Leu
                580                 585                 590

Gln Lys Met Leu Tyr Thr Glu Asp Glu Ile Met Ser Leu Phe Pro Asn
                595                 600                 605

Gly Ser His Ala Phe Arg Val Arg Ala Thr Ile Arg Val Leu Ser Trp
            610                 615                 620

Gln Gly Thr Asn Asp Cys Gly Asp Phe Glu Lys Ile Tyr Leu Tyr Asp
625                 630                 635                 640
```

```
Pro Val Ser Gln Glu Ala Gln Val Glu Leu Arg Lys Asp Leu Ala Met
                645                 650                 655

Phe Ser Lys Glu Val Met Asn Arg Asn Ser Lys Arg Phe Ile Pro Tyr
            660                 665                 670

Lys Tyr Leu Asp Pro Asn Tyr Val Pro Asn Ala Ile Ser Ile
        675                 680                 685

<210> SEQ ID NO 5
<211> LENGTH: 40
<212> TYPE: DNA
<213> ORGANISM: Artificial Sequence
<220> FEATURE:
<223> OTHER INFORMATION: PKLOX1 Forward Primer

<400> SEQUENCE: 5 tgtatttttca gggcgccatg gcgccaatta aggaaaagaa                    40

<210> SEQ ID NO 6
<211> LENGTH: 43
<212> TYPE: DNA
<213> ORGANISM: Artificial Sequence
<220> FEATURE:
<223> OTHER INFORMATION: PKLOX1 Reverse Primer

<400> SEQUENCE: 6
agtgagctcg tcgacgtagg ctatacactg atggcatttg aa                  43

<210> SEQ ID NO 7
<211> LENGTH: 40
<212> TYPE: DNA
<213> ORGANISM: Artificial Sequence
<220> FEATURE:
<223> OTHER INFORMATION: PKLOX2 Forward Primer

<400> SEQUENCE: 7 tgtatttttca gggcgccatg gtagcgctgc gctgcttcaa                    40

<210> SEQ ID NO 8
<211> LENGTH: 43
<212> TYPE: DNA
<213> ORGANISM: Artificial Sequence
<220> FEATURE:
<223> OTHER INFORMATION: PKLOX2 Reverse Primer

<400> SEQUENCE: 8
agtgagctcg tcgacgtagg ctaaatactt attgcatttg aa                  43

<210> SEQ ID NO 9
<211> LENGTH: 78
<212> TYPE: DNA
<213> ORGANISM: Artificial Sequence
<220> FEATURE:
<223> OTHER INFORMATION: 6xHis + TEV Site
<220> FEATURE:
<221> NAME/KEY: CDS
<222> LOCATION: (1)..(78)

<400> SEQUENCE: 9 atg tcg tac tac cat cac cat cac cat cac gat tac gat atc cca acg    48
Met Ser Tyr Tyr His His His His His His Asp Tyr Asp Ile Pro Thr
1               5                   10                  15 acc gaa aac ctg tat ttt cag ggc gcc atg                            78
Thr Glu Asn Leu Tyr Phe Gln Gly Ala Met
            20                  25
```

```
<210> SEQ ID NO 10
<211> LENGTH: 26
<212> TYPE: PRT
<213> ORGANISM: Artificial Sequence
<220> FEATURE:
<223> OTHER INFORMATION: Synthetic Construct

<400> SEQUENCE: 10

Met Ser Tyr Tyr His His His His His His Asp Tyr Asp Ile Pro Thr
1               5                   10                  15

Thr Glu Asn Leu Tyr Phe Gln Gly Ala Met
            20                  25
```